United States Patent
Djupesland

(10) Patent No.: US 9,522,243 B2
(45) Date of Patent: Dec. 20, 2016

(54) NASAL DEVICES

(71) Applicant: OptiNose AS, Oslo (NO)

(72) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 0 days.

(21) Appl. No.: 14/816,247

(22) Filed: Aug. 3, 2015

(65) Prior Publication Data

US 2016/0193435 A1   Jul. 7, 2016

Related U.S. Application Data

(63) Continuation of application No. 13/785,694, filed on Mar. 5, 2013, now Pat. No. 9,132,249, which is a continuation of application No. 13/244,499, filed on Sep. 25, 2011, now abandoned, which is a continuation of application No. 12/339,716, filed on Dec. 19, 2008, now Pat. No. 8,047,202, which is a continuation of application No. 10/520,380, filed as application No. PCT/IB03/03274 on Jul. 2, 2003, now Pat. No. 7,481,218.

(30) Foreign Application Priority Data

Jul. 2, 2002  (GB) ...................... 0215270

(51) Int. Cl.
*A61M 15/08*   (2006.01)
*A61M 15/00*   (2006.01)

(52) U.S. Cl.
CPC .......... *A61M 15/08* (2013.01); *A61M 15/009* (2013.01); *A61M 15/0021* (2014.02); *A61M 15/0051* (2014.02); *A61M 15/0091* (2013.01); *A61M 15/0098* (2014.02); *A61M 2202/04* (2013.01); *A61M 2202/064* (2013.01); *A61M 2202/30* (2013.01); *A61M 2209/06* (2013.01)

(58) Field of Classification Search
CPC .................. A61M 15/08; A61M 15/0021; A61M 15/0091; A61M 15/0098; A61M 2002/30
See application file for complete search history.

(56) References Cited

U.S. PATENT DOCUMENTS 605,436 A   6/1898   Kellogg
642,748 A   2/1900   Manners
(Continued)

FOREIGN PATENT DOCUMENTS

DE   19825434   8/1999
EP   0779078    6/1997
(Continued)

OTHER PUBLICATIONS

English-Language Abstract of DE 19825434.
(Continued)

*Primary Examiner* — Kristen Matter
(74) *Attorney, Agent, or Firm* — Finnegan, Henderson, Farabow, Garrett & Dunner, LLP

(57) ABSTRACT

A nasal delivery device and a method of delivering substance to a nasal airway of a subject can be used for mass treatment, especially mass vaccination. The delivery device can include an interface unit, as a replaceable unit, having at least one nosepiece unit for fitting to a respective nostril of a subject, a nozzle from which substance is in use delivered, and at least one delivery unit having a substance supply unit for delivering substance to the nozzle of the at least one nosepiece unit. The delivery device can also include an actuation unit for actuating the at least one delivery unit of the interface unit.

17 Claims, 15 Drawing Sheets

(56) References Cited

U.S. PATENT DOCUMENTS

| | | | |
|---|---|---|---|
| 746,749 A | 12/1903 | Seidel | |
| 2,470,297 A | 5/1949 | Fields | |
| 3,730,180 A | 5/1973 | Davison | |
| 3,802,431 A | 4/1974 | Farr | |
| 4,509,196 A | 4/1985 | Sak et al. | |
| 5,355,872 A | 10/1994 | Riggs et al. | |
| 5,501,373 A | 3/1996 | Galli | |
| 5,797,392 A | 8/1998 | Keldmann et al. | |
| 5,899,202 A | 5/1999 | Ohki et al. | |
| 6,269,810 B1 | 8/2001 | Brooker et al. | |
| 6,302,101 B1 | 10/2001 | Py | |
| 6,648,848 B1 | 11/2003 | Keldmann et al. | |
| 6,681,767 B1 | 1/2004 | Patton et al. | |
| 6,708,846 B1 | 3/2004 | Fuchs et al. | |
| 6,715,485 B1 | 4/2004 | Djupesland | |
| D530,815 S | 10/2006 | Murphy et al. | |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland et al. | |
| 7,975,690 B2 | 7/2011 | Djupesland | |
| 8,047,202 B2 | 11/2011 | Djupesland | |
| 8,146,589 B2 | 4/2012 | Djupesland | |
| 8,171,929 B2 | 5/2012 | Djupesland et al. | |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,590,530 B2 | 11/2013 | Djupesland et al. | |
| 8,596,278 B2 | 12/2013 | Djupesland | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2 | 3/2015 | Djupesland et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,108,015 B2 | 8/2015 | Djupesland | |
| 9,119,932 B2 | 9/2015 | Djupesland | |
| 9,132,249 B2 | 9/2015 | Djupesland | |
| 9,144,652 B2 | 9/2015 | Djupesland et al. | |
| 9,168,341 B2 | 10/2015 | Djupesland | |
| 9,205,208 B2 | 12/2015 | Djupesland | |
| 9,205,209 B2 | 12/2015 | Djupesland | |
| 9,272,104 B2 | 3/2016 | Djupesland | |
| D759,805 S | 6/2016 | Djupesland | |
| D761,951 S | 7/2016 | Djupesland | |
| 9,452,272 B2 | 9/2016 | Djupesland et al. | |
| 9,468,727 B2 | 10/2016 | Djupesland | |
| 2004/0024330 A1 | 2/2004 | Djupesland et al. | |
| 2004/0112378 A1 | 6/2004 | Djupesland | |
| 2004/0112379 A1 | 6/2004 | Djupesland | |
| 2004/0112380 A1 | 6/2004 | Djupesland | |
| 2004/0149289 A1 | 8/2004 | Djupesland | |
| 2004/0153033 A1 | 8/2004 | Mazzoni | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0096589 A1 | 5/2006 | Djupesland | |
| 2006/0107957 A1 | 5/2006 | Djupesland | |
| 2006/0124125 A1 | 6/2006 | Gonda et al. | |
| 2006/0169278 A1 | 8/2006 | Djupesland et al. | |
| 2006/0174886 A1 | 8/2006 | Curti et al. | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland et al. | |
| 2008/0223363 A1 | 9/2008 | Djupesland | |
| 2008/0289629 A1 | 11/2008 | Djupesland et al. | |
| 2009/0101146 A1 | 4/2009 | Djupesland | |
| 2009/0293873 A1 | 12/2009 | Djupesland et al. | |
| 2009/0304802 A1 | 12/2009 | Djupesland et al. | |
| 2009/0314293 A1 | 12/2009 | Djupesland | |
| 2009/0320832 A1 | 12/2009 | Djupestand | |
| 2010/0035805 A1 | 2/2010 | Hafner | |
| 2010/0051022 A1 | 3/2010 | Djupesland et al. | |
| 2010/0057047 A1 | 3/2010 | Djupesland et al. | |
| 2010/0242959 A1 | 9/2010 | Djupesland et al. | |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0023869 A1 | 2/2011 | Djupesland | |
| 2011/0053827 A1 | 3/2011 | Hafner | |
| 2011/0088690 A1 | 4/2011 | Djupesland et al. | |
| 2011/0088691 A1 | 4/2011 | Djupesland | |
| 2011/0114087 A1 | 5/2011 | Djupesland et al. | |
| 2011/0126830 A1 | 6/2011 | Djupesland et al. | |
| 2011/0259329 A1 | 10/2011 | Djupesland et al. | |
| 2011/0318345 A1 | 12/2011 | Djupesland | |
| 2012/0000459 A1 | 1/2012 | Djupesland | |
| 2012/0006323 A1 | 1/2012 | Djupesland | |
| 2012/0073571 A1 | 3/2012 | Djupesland | |
| 2012/0090608 A1 | 4/2012 | Djupesland et al. | |
| 2012/0260915 A1 | 10/2012 | Djupesland | |
| 2013/0098362 A1 | 4/2013 | Djupesland et al. | |
| 2013/0125889 A1 | 5/2013 | Djupesland et al. | |
| 2013/0327320 A1 | 12/2013 | Djupesland | |
| 2014/0018295 A1 | 1/2014 | Djupesland | |
| 2014/0041660 A1 | 2/2014 | Djupesland et al. | |
| 2014/0060536 A1 | 3/2014 | Djupesland | |
| 2014/0073562 A1 | 3/2014 | Djupesland | |
| 2014/0144442 A1 | 5/2014 | Djupesland et al. | |
| 2014/0144443 A1 | 5/2014 | Djupesland et al. | |
| 2014/0166008 A1 | 6/2014 | Djupesland | |
| 2014/0202456 A1 | 7/2014 | Djupesland | |
| 2014/0246022 A1 | 9/2014 | Djupesland et al. | |
| 2015/0007811 A1 | 1/2015 | Djupesland et al. | |
| 2015/0013670 A1 | 1/2015 | Djupesland et al. | |
| 2015/0013677 A1 | 1/2015 | Djupesland et al. | |
| 2015/0053201 A1 | 2/2015 | Djupesland et al. | |
| 2015/0090259 A1 | 4/2015 | Djupesland et al. | |
| 2015/0101605 A1 | 4/2015 | Djupesland et al. | |
| 2015/0144129 A1 | 5/2015 | Djupesland et al. | |
| 2015/0165139 A1 | 6/2015 | Hafner | |
| 2015/0182709 A1 | 7/2015 | Djupesland | |
| 2015/0246194 A1 | 9/2015 | Djupesland et al. | |
| 2015/0367090 A1 | 12/2015 | Djupesland et al. | |
| 2015/0367091 A1 | 12/2015 | Djupesland et al. | |
| 2016/0001022 A1 | 1/2016 | Djupesland et al. | |
| 2016/0045687 A1 | 2/2016 | Djupesland | |
| 2016/0051778 A1 | 2/2016 | Djupesland et al. | |
| 2016/0074603 A1 | 3/2016 | Djupesland et al. | |
| 2016/0082206 A1 | 3/2016 | Djupesland et al. | |
| 2016/0082207 A1 | 3/2016 | Djupesland et al. | |
| 2016/0166788 A1 | 6/2016 | Djupesland et al. | |
| 2016/0184537 A1 | 6/2016 | Djupesland | |
| 2016/0193435 A1 | 7/2016 | Djupesland | |
| 2016/0250408 A1 | 9/2016 | Djupesland | |
| 2016/0263334 A1 | 9/2016 | Djupesland | |
| 2016/0279357 A1 | 9/2016 | Djupesland | |

FOREIGN PATENT DOCUMENTS

| | | |
|---|---|---|
| EP | 1180378 | 11/2010 |
| WO | WO 92/21404 | 12/1992 |
| WO | WO 96/22802 | 8/1996 |

| | | |
|---|---|---|
| WO | WO 98/53869 | 12/1998 |
| WO | WO 99/58180 | 11/1999 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Cindy H. Dubin, *Nothing to Sneeze At*, Pharmaceutical Formulation & Quality Magazine (Jan. 29, 2003).

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).

Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

NASAL DEVICES

This is a continuation application of U.S. application Ser. No. 13/785,694 filed Mar. 5, 2013, that is a continuation of U.S. Ser. No. 13/244,499 filed Sep. 25, 2011, now abandoned, that is a continuation of U.S. Ser. No. 12/339,716 filed Dec. 19, 2008, now U.S. Pat. No. 8,047,202, that is the continuation of U.S. Ser. No. 10/520,380 filed Oct. 13, 2005, now U.S. Pat. No. 7,481,218, that is the national stage entry of PCT/IB2003/003274 filed Jul. 2, 2003, which claims priority to GB 0215270 filed on Jul. 2, 2002, the entire contents of each of which are incorporated herein by reference.

The present invention relates to a nasal delivery device for and a method of delivering a substance, in particular one of a liquid, as a suspension or solution, or a powder containing a medicament, especially systemic or topical pharmaceuticals, or a vaccine to the nasal airway of a subject, in particular for the mass treatment, especially vaccination, of subjects.

Referring to FIG. 1, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery also provides for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

Nasal delivery also further provides an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, nasal delivery also further provides for the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Still furthermore, and a prime focus of the present invention is the nasal delivery of vaccines. The nasal delivery device of the present invention has been developed with the particular aim of providing a delivery device for the mass treatment, in particular the mass vaccination, of subjects.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide improved nasal delivery devices and nasal delivery methods for providing for the delivery of substance to subjects, in particular for the mass treatment, especially vaccination, of subjects.

In one aspect the present invention provides a nasal delivery device for delivering substance to a nasal airway of a subject, comprising: an interface unit, as a replaceable unit, including at least one nosepiece unit for fitting to a respective nostril of a subject and including a nozzle from which substance is in use delivered, and at least one delivery unit including a substance supply unit for delivering substance to the nozzle of the at least one nosepiece unit; and an actuation unit for actuating the at least one delivery unit of the interface unit.

Preferably, the interface unit comprises a disposable unit.

Preferably, the interface unit comprises a single integral unit.

Preferably, the interface unit is packaged in protective packaging.

In one embodiment the delivery device comprises: a plurality of interface units attached to a belt such as to allow for successive attachment of the interface units to the actuation unit.

Preferably, the actuation unit is configured successively to provide the interface units thereto through use of the belt as a guide.

Preferably, the substance supply unit comprises a substance pump unit for delivering substance, the substance pump unit including a chamber containing substance and a piston member which is movable in the chamber to deliver a flow of substance from the chamber.

In one embodiment the substance comprises a liquid.

In another embodiment the substance comprises a powder.

Preferably, the interface unit includes a mouthpiece unit including a mouthpiece into which a subject in use exhales.

In one embodiment the mouthpiece is fluidly connected to the at least one nosepiece unit such as to provide an air flow therethrough on exhalation by a subject into the mouthpiece.

In one embodiment the at least one delivery unit includes a gas supply unit for supplying a gas flow through the at least one nosepiece unit.

Preferably, the gas supply unit comprises a gas pump unit for delivering a gas flow, the gas pump unit comprising a cylinder and a piston member which is movable in the cylinder to deliver a gas flow through the at least one nosepiece unit.

In one embodiment the at least one delivery unit is configured such that the gas supply unit initiates supply of a gas flow prior to actuation of the substance supply unit to deliver substance.

In another embodiment the actuation unit includes a gas supply unit for supplying a gas flow through the at least one nosepiece unit.

In one embodiment the actuation unit is configured such that the gas supply unit initiates supply of a gas flow prior to actuation of the substance supply unit to deliver substance.

Preferably, the at least one delivery unit is actuated in response to exhalation by the subject.

In one embodiment the actuation unit includes a detection unit for detecting exhalation by a subject, at least one drive unit for actuating the at least one delivery unit, and a control unit for actuating the at least one drive unit in response to detecting exhalation by the subject.

In one embodiment the detection unit includes a pressure sensor for detecting a pressure in the mouthpiece, and the control unit is configured to actuate the at least one drive unit in response to detection of a predeterminable pressure by the detection unit.

In another embodiment the detection unit includes a flow sensor for detecting a flow rate through the mouthpiece, and the control unit is configured to actuate the at least one drive unit in response to detection of a predeterminable flow rate by the detection unit.

In another embodiment the actuation unit includes at least one drive unit for actuating the at least one delivery unit, and a trigger mechanism for actuating the at least one drive unit in response to exhalation by the subject.

In one embodiment the trigger mechanism is configured to actuate the at least one drive unit in response to generation of a predeterminable pressure in the mouthpiece.

In another embodiment the trigger mechanism is configured to actuate the at least one drive unit in response to detection of a predeterminable flow rate through the mouthpiece.

Preferably, the interface unit includes first and second nosepiece units for fitting to respective nostrils of the subject, and first and second delivery units, each including a substance supply unit for delivering substance through the respective nosepiece unit.

More preferably, the actuation unit is configured to actuate the first and second delivery units in succession such that substance is first delivered into one nasal cavity and subsequently into the other nasal cavity.

In another aspect the present invention provides a method of delivering substance to a nasal airway of a subject, comprising the steps of providing an interface unit, as a replaceable unit, to an actuation unit, the interface unit including at least one nosepiece unit for fitting to a respective nostril of a subject and including a nozzle from which substance is delivered, and at least one delivery unit including a substance supply unit for delivering substance to the nozzle of the at least one nosepiece unit, and the actuation unit being configured to actuate the at least one delivery unit of the interface unit; fitting the interface unit to a subject; and actuating the actuation unit to actuate the at least one delivery unit such as to deliver substance to a nasal airway of the subject.

Preferably, the interface unit comprises a disposable unit.

Preferably, the interface unit comprises a single integral unit.

Preferably, the interface unit is packaged in protective packaging, and, prior to the fitting step, the method further comprises the step of: opening the protective packaging.

In one embodiment a plurality of interface units are attached to a belt, and, in the interface unit providing step, a subsequent one of the interface units is provided to the actuation unit.

Preferably, in the interface unit providing step, the actuation unit advances the belt of interface units such as to provide a subsequent one of the interface units thereto.

Preferably, the substance supply unit comprises a substance pump unit for delivering substance, and the substance pump unit includes a chamber containing substance and a piston member which is moved in the chamber to deliver a flow of substance from the chamber.

In one embodiment the substance comprises a liquid.

In another embodiment the substance comprises a powder.

Preferably, the interface unit includes a mouthpiece unit including a mouthpiece, and, prior to the actuation unit actuating step, the method further comprises the step of: the subject exhaling into the mouthpiece.

In one embodiment the mouthpiece is fluidly connected to the at least one nosepiece unit such as to provide an air flow therethrough on exhalation by the subject into the mouthpiece.

In one embodiment the at least one delivery unit includes a gas supply unit for supplying a gas flow, and the method further comprises the step of: actuating the gas supply unit to supply a gas flow through the at least one nosepiece unit.

Preferably, the gas supply unit comprises a gas pump unit for delivering a gas flow, and the gas pump unit comprises a cylinder and a piston member which is moved in the cylinder to deliver a gas flow through the at least one nosepiece unit.

In one embodiment, for each delivery unit, the supply of a gas flow is initiated prior to the delivery of substance.

In another embodiment the actuation unit includes a gas supply unit for supplying a gas flow, and the method further comprises the step of actuating the gas supply unit to supply a gas flow through the at least one nosepiece unit.

In one embodiment, for each delivery unit, the supply of a gas flow is initiated prior to the delivery of substance.

Preferably, the at least one delivery unit is actuated in response to exhalation by the subject.

In one embodiment the actuation unit includes a detection unit for detecting exhalation by the subject and at least one drive unit for actuating the at least one delivery unit; and the actuation unit actuating step comprises the step of: actuating the at least one drive unit in response to the detection unit detecting exhalation by the subject.

In one embodiment the detection unit includes a pressure sensor for detecting a pressure in the mouthpiece, and the at least one drive unit is actuated in response to detection of a predeterminable pressure by the detection unit.

In another embodiment the detection unit includes a flow sensor for detecting a flow rate through the mouthpiece, and the at least one drive unit is actuated in response to detection of a predeterminable flow rate by the detection unit.

In another embodiment the actuation unit includes at least one drive unit for actuating the at least one delivery unit and a trigger mechanism for actuating the at least one drive unit in response to exhalation by the subject; and the actuation unit actuating step comprises the step of: actuating the trigger mechanism to actuate the at least one drive unit in response to exhalation by the subject.

In one embodiment the trigger mechanism is configured to actuate the at least one drive unit in response to generation of a predeterminable pressure in the mouthpiece.

In another embodiment the trigger mechanism is configured to actuate the at least one drive unit in response to detection of a predeterminable flow rate through the mouthpiece.

Preferably, the interface unit includes first and second nosepiece units for fitting to respective nostrils of the subject, and first and second delivery units, each including a substance supply unit for delivering substance through the respective nosepiece unit, and the actuation unit actuating step comprises the step of: actuating the actuation unit to actuate the first and second delivery units such as to deliver substance to the respective nasal cavities of the subject.

In one embodiment the first and second delivery units are actuated in succession such that substance is first delivered into one nasal cavity and subsequently into the other nasal cavity.

Preferably, the method is for the mass treatment of subjects, in particular the mass vaccination of subjects.

In a further aspect the present invention provides a nasal delivery component, as a disposable component, comprising at least one nosepiece unit for fitting to a respective nostril of a subject and including a nozzle from which substance is in use delivered, and at least one delivery unit including a substance supply unit for delivering substance to the nozzle of the at least one nosepiece unit.

Preferably, the delivery component is an interface unit for attachment to an actuation unit utilized in actuating the at least one delivery unit.

In one embodiment a plurality of delivery units are attached to a belt such as to allow for successive attachment to the actuation unit.

Preferably, the at least one delivery unit is manually actuatable absent an actuation unit.

Preferably, the delivery component is packaged in protective packaging.

Preferably, the substance supply unit comprises a substance pump unit for delivering substance, the substance pump unit including a chamber containing substance and a piston member which is movable in the chamber to deliver a flow of substance from the chamber.

In one embodiment the substance is a liquid.

In another embodiment the substance is a powder.

Preferably, the delivery component further comprises a mouthpiece unit including a mouthpiece into which the subject in use exhales.

In one embodiment the mouthpiece is fluidly connected to the at least one nosepiece unit such as to provide an air flow therethrough on exhalation by the subject into the mouthpiece.

In one embodiment the at least one delivery unit includes a gas supply unit for supplying a gas flow through the at least one nosepiece unit.

Preferably, the gas supply unit comprises a gas pump unit for delivering a gas flow, the gas pump unit including a cylinder and a piston member which is movable in the cylinder to deliver a gas flow through the respective nosepiece unit.

In one embodiment the at least one delivery unit is configured such that the gas supply unit initiates supply of a gas flow prior to the substance supply unit delivering substance.

Preferably, the delivery unit comprises first and second nosepiece units for fitting to respective nostrils of the subject, and first and second delivery units, each for delivering substance through a respective one of the first and second nosepiece units.

Preferably, the delivery component is configured such as to be separable between the first and second nosepiece units, and thereby provide two delivery units which are each separably operable.

In a yet further aspect the present invention provides an actuation unit for receiving and actuating an interface unit, as a replaceable unit, to deliver substance to a nasal airway of a subject, the interface unit including at least one nosepiece unit for fitting to a respective nostril of a subject and including a nozzle from which substance is in use delivered, and at least one delivery unit including a substance supply unit for delivering substance to the nozzle of the at least one nosepiece unit, the actuation unit comprising: at least one drive unit for actuating the at least one delivery unit of the interface unit.

Preferably, the interface unit includes a mouthpiece unit including a mouthpiece into which the subject in use exhales.

In one embodiment the mouthpiece is fluidly connected to the at least one nosepiece unit such as to provide an air flow therethrough on exhalation by the subject into the mouthpiece.

In one embodiment the actuation unit further comprises: a detection unit for detecting exhalation by the subject into the mouthpiece; and a control unit for actuating the at least one drive unit in response to detecting exhalation by the subject.

In one embodiment the detection unit includes a pressure sensor for detecting a pressure in the mouthpiece, and the control unit is configured to actuate the at least one drive unit in response to detection of a predeterminable pressure by the detection unit.

In another embodiment the detection unit includes a flow sensor for detecting a flow rate through the mouthpiece, and the control unit is configured to actuate the at least one drive unit in response to detection of a predeterminable flow rate by the detection unit.

In another embodiment the actuation unit further comprises: a trigger mechanism for actuating the at least one delivery unit in response to exhalation by the subject into the mouthpiece.

In one embodiment the trigger mechanism is configured to actuate the at least one drive unit in response to generation of a predeterminable pressure in the mouthpiece.

In another embodiment the trigger mechanism is configured to actuate the at least one drive unit in response to detection of a predeterminable flow rate through the mouthpiece.

In one embodiment the at least one delivery unit includes a gas supply unit for supplying a gas flow through the at least one nosepiece unit.

In another embodiment the actuation unit further comprises: a gas supply unit for supplying a gas flow through the at least one nosepiece unit.

In one embodiment a plurality of interface units are attached to a belt, and the actuation unit is configured to advance the belt such as successively to provide interface units thereto.

Preferably, the belt to which the interface units are attached is utilized as a guide.

Preferably, the interface unit includes first and second nosepiece units for fitting to respective nostrils of the subject, and first and second delivery units, each for delivering substance through respective ones of the first and second nosepiece units, and the actuation unit further comprises: first and second drive units for actuating respective ones of the delivery units of the interface unit.

More preferably, the first and second drive units are configured to actuate the substance supply units in succession, and thereby deliver substance first into one nasal cavity and subsequently into the other nasal cavity.

Preferred embodiments of the present invention will now be described hereinbelow by way of example only with reference to the accompanying drawings, in which:

FIG. 1 schematically illustrates the anatomy of the upper respiratory tract of a human subject;

Figure 1:
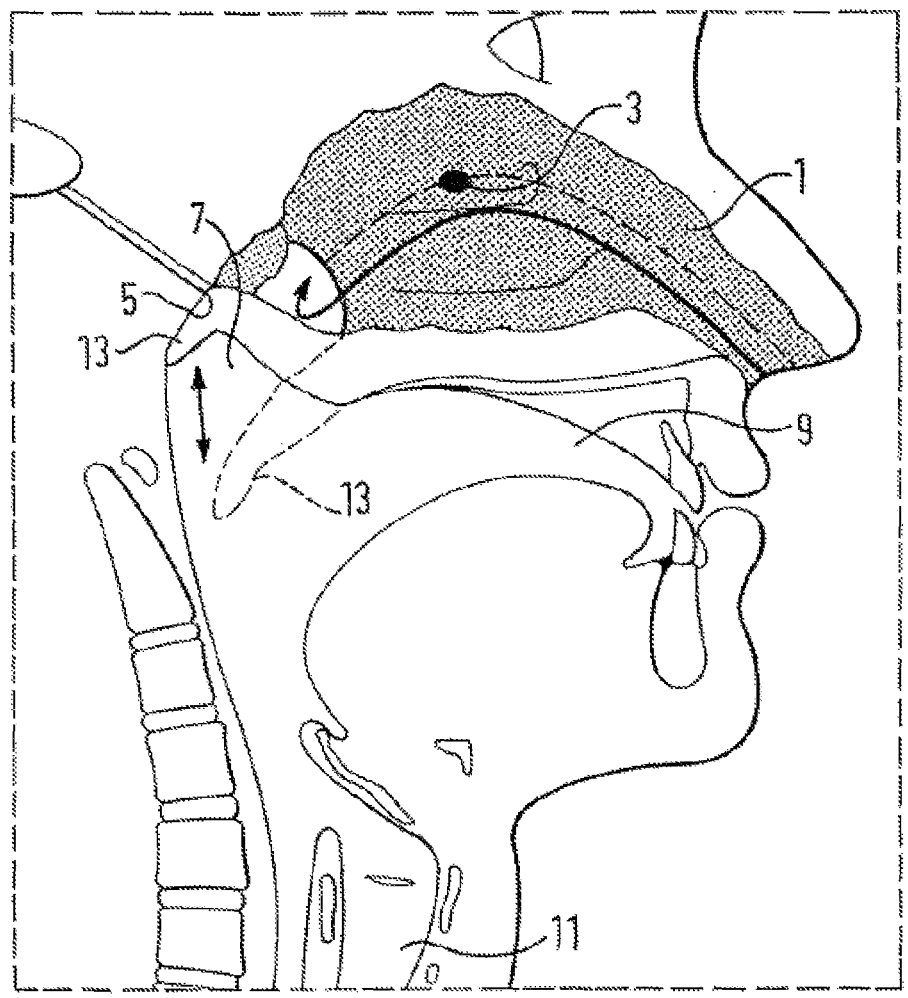
Figure 5:
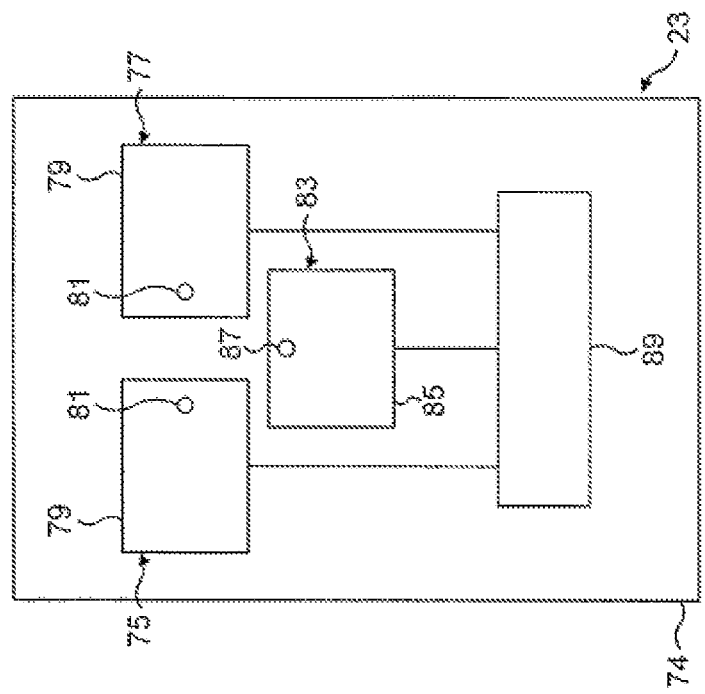
Figure 2:
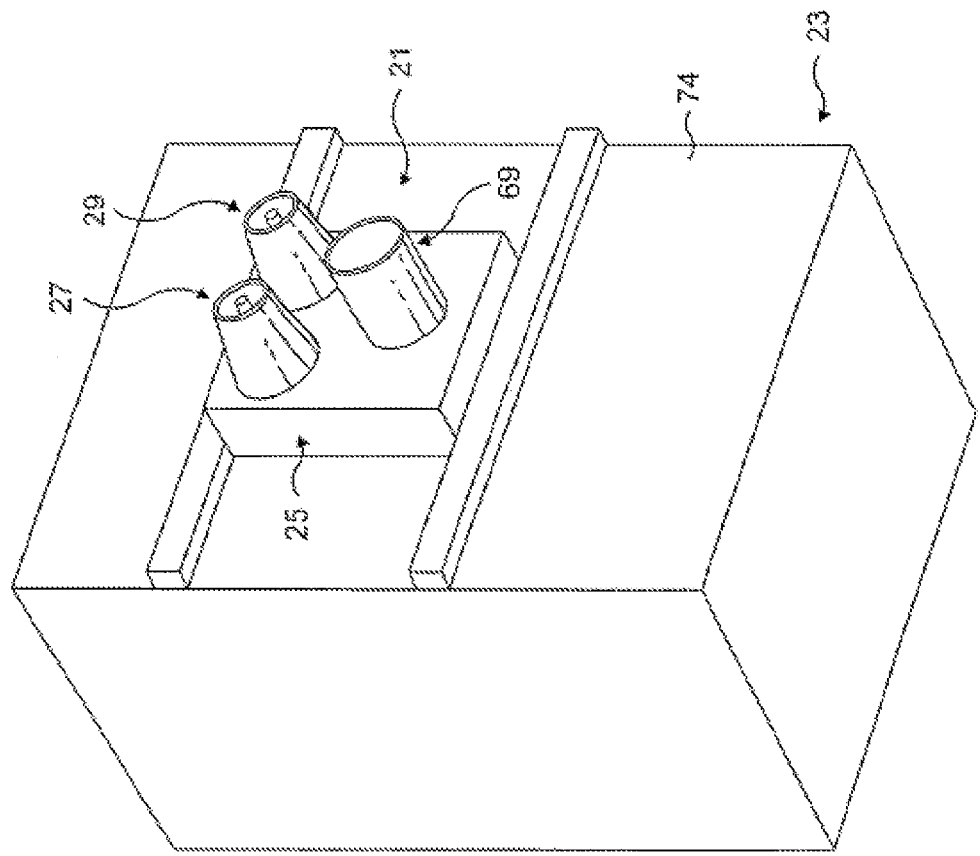
FIG. 2 illustrates a nasal delivery device in accordance with a first embodiment of the present invention.
Figure 4:
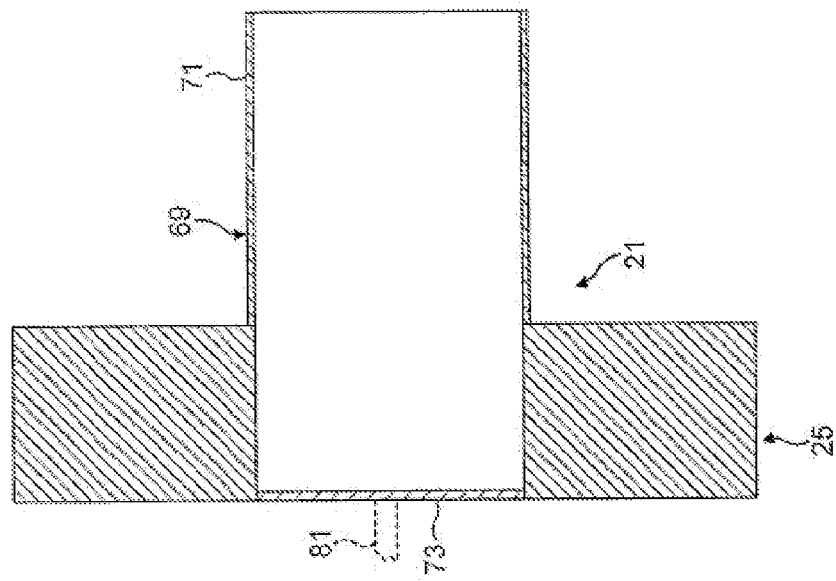
FIG. 4 illustrates a sectional view through the mouthpiece unit of the interface unit of the delivery device of FIG. 2.
Figure 3:
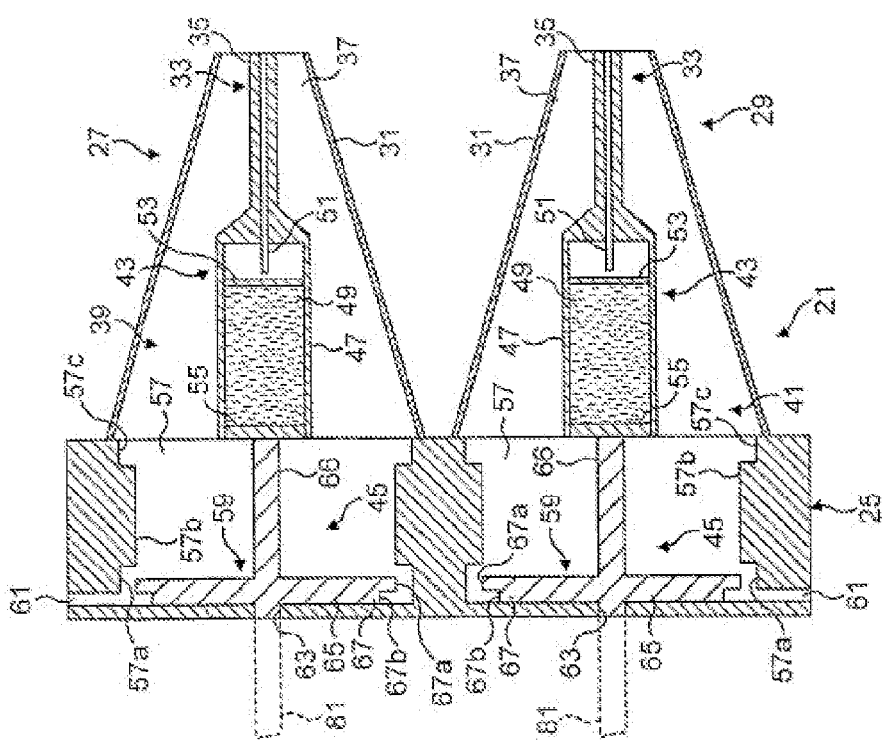
FIG. 3 illustrates a sectional view through the nosepiece units and delivery units of the interface unit of the delivery device of FIG. 2.
Figure 7A:
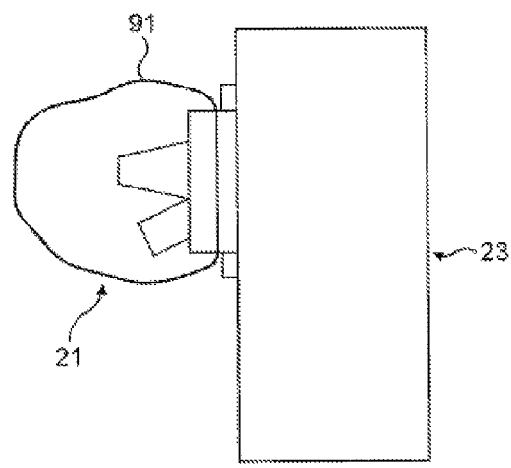
Figure 8:
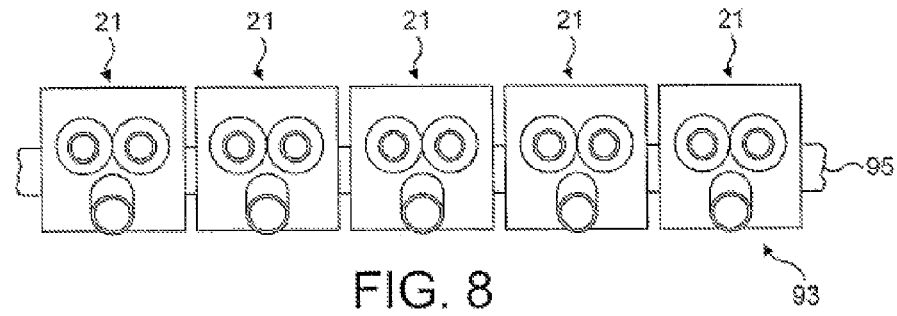
Figure 9:
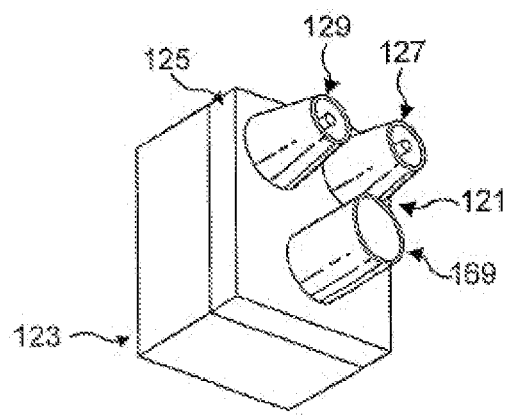
Figure 11:
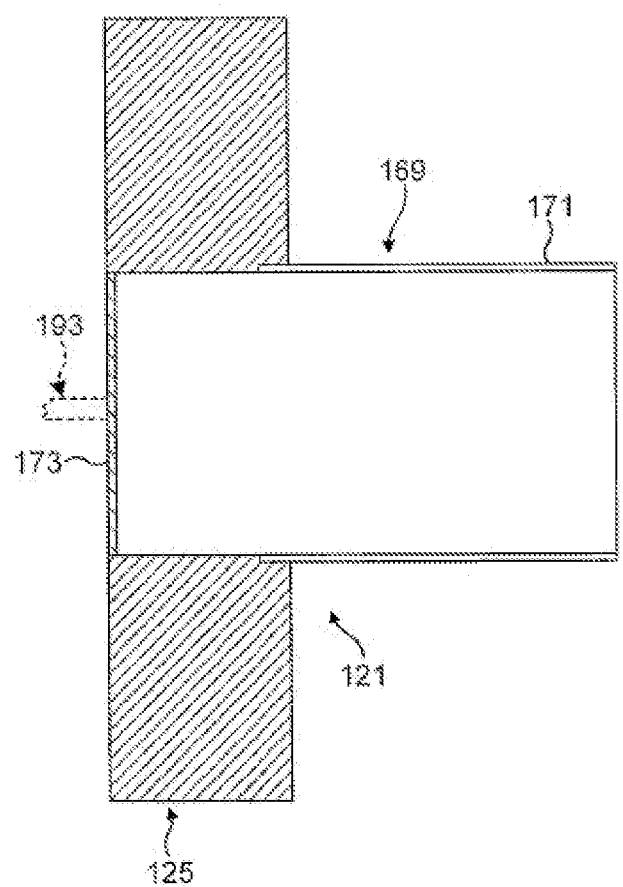
Figure 10:
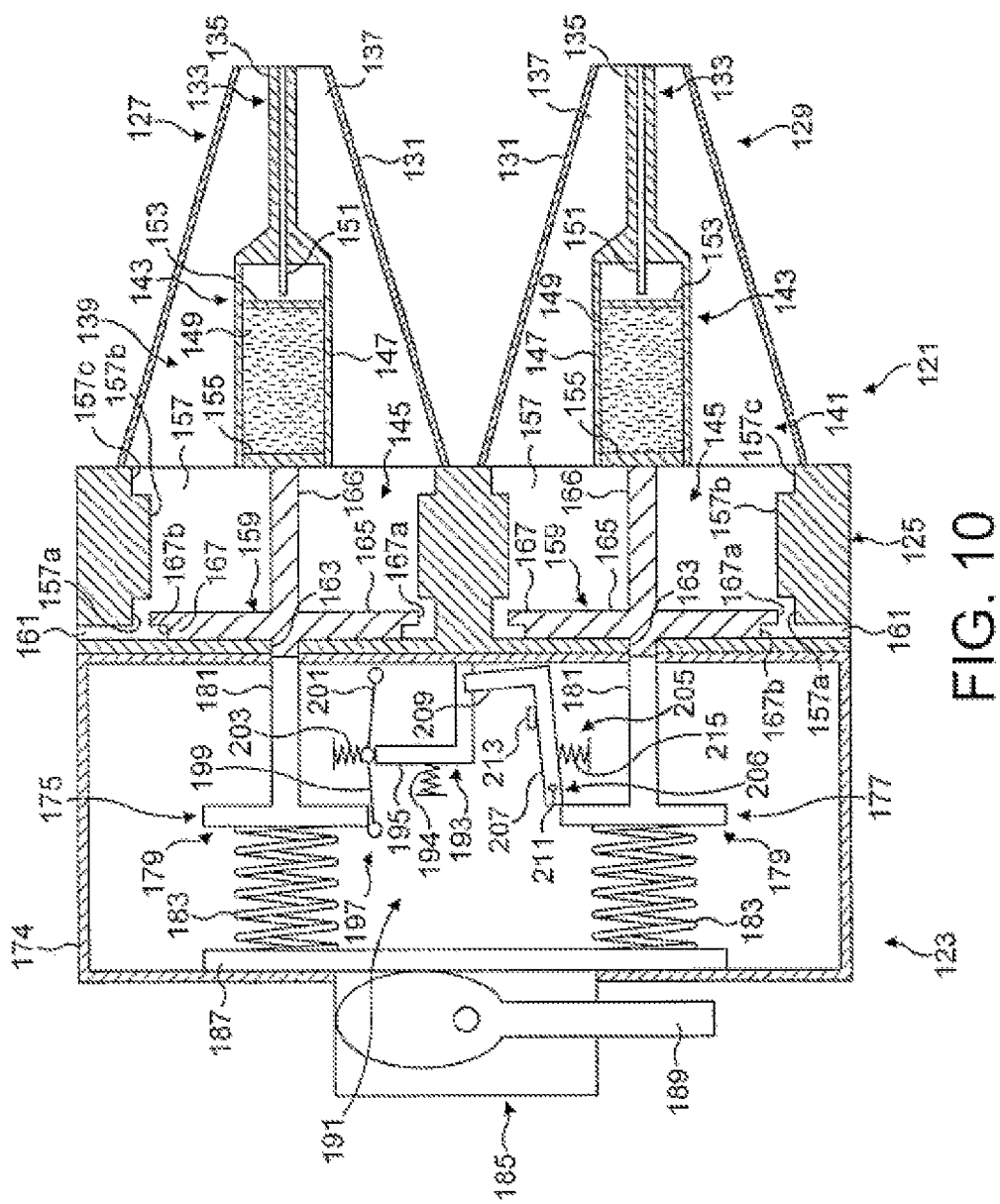

FIG. 5 schematically represents the actuation unit of the delivery device of FIG. 2;

FIGS. 6(a) to (d) illustrate the operation of the delivery device of FIG. 2;

FIGS. 7(a) and (b) illustrate one modification of the interface unit of the delivery device of FIG. 2;

FIG. 8 illustrates an interface unit supply as another modification of the delivery device of FIG. 2;

FIG. 9 illustrates a nasal delivery device in accordance with a second embodiment of the present invention;

FIG. 10 illustrates a sectional view through the nosepiece units and delivery units of the interface unit and the actuation unit of the delivery device of FIG. 9;

FIG. 11 illustrates a sectional view through the mouthpiece unit of the interface unit of the delivery device of FIG. 8; and FIGS. 12(a) to (e) illustrate the operation of the delivery device of FIG. 9.

FIGS. 2 to 6 illustrate a nasal delivery device in accordance with a first embodiment of the present invention.

The delivery device comprises an interface unit 21 for fitting to a subject and containing the substance to be delivered, and an actuation unit 23 to which the interface unit 21 is attached to enable the delivery of the substance from the interface unit 21 on exhalation by the subject. In this embodiment the interface unit 21 is a disposable component and the means of attachment of the interface unit 21 to the actuation unit 23 is such as to allow for the easy, repeated attachment of interface units 21 to allow for the treatment of large numbers of subjects, such as in the mass vaccination of subjects.

The interface unit 21 comprises a main body 25 for attachment to the actuation unit 23, in this embodiment as a sliding fit. In an alternative embodiment the main body 25 could be configured to be a clip fit to the actuation unit 23. In this embodiment the means of attachment of the interface unit 21 to the actuation unit 23 is configured, here by the provision of differently-shaped slide features, such as to provide for the attachment of the interface unit 21 to the actuation unit 23 in the correct orient.

The interface unit 21 further comprises first and second nosepiece units 27, 29 for fitting to respective ones of the nostrils of a subject.

The nosepiece units 27, 29 each comprise a cuff member 31, in this embodiment a frusto-conical element, for positioning the respective nosepiece unit 27, 29 in a nasal cavity of the subject and providing a fluid-tight seal therewith, and an outlet unit 33 for delivering substance into the respective nasal cavity of the subject.

Each outlet unit 33 comprises a nozzle 35 from which substance is delivered into the respective nasal cavity of the subject, and a delivery channel 37 through which a gas flow, in this embodiment separate from the exhalation breath of the subject, is delivered to entrain the substance delivered from the nozzle 35.

In this embodiment the nozzle 35 is configured to provide an aerosol spray. In an alternative embodiment, for the delivery of a liquid, the nozzle 35 could be configured to deliver a liquid jet as a column of liquid.

In this embodiment the nozzle 35 is disposed in the delivery channel 37 co-axially with the same. In this embodiment the delivery channel 37 is an annular channel which surrounds the nozzle 35 such as to define an annular gas flow which entrains the substance delivered from the nozzle 35.

The interface unit 21 further comprises first and second delivery units 39, 41 which are fluidly connected to respective ones of the first and second nosepiece units 27, 29. The delivery units 39, 41 each comprise a substance supply unit 43 for delivering a metered dose of a substance to the respective nozzle 35 and a gas supply unit 45 for delivering a metered volume of a gas, in this embodiment separate to the exhalation breath of the subject, as a gas flow through the respective delivery channel 37. In preferred embodiments the substance comprises a medicament, especially systemic or topical pharmaceuticals, or a vaccine.

In this embodiment each substance supply unit 43 comprises a liquid delivery pump for delivering a metered dose of a substance on actuation thereof, as one of an aerosol spray or a liquid jet as a column of liquid from the respective nozzle 35.

Each substance supply unit 43 comprises a piston unit which comprises a cylinder 47 which defines a chamber 49 and into one, forward end of which a hollow needle 51 extends as an extension of the respective nozzle 35.

Each substance supply unit 43 further comprises first and second pistons 53, 55 which contain a volume of substance therebetween and are movably disposed within the chamber 49.

Figure 6A:
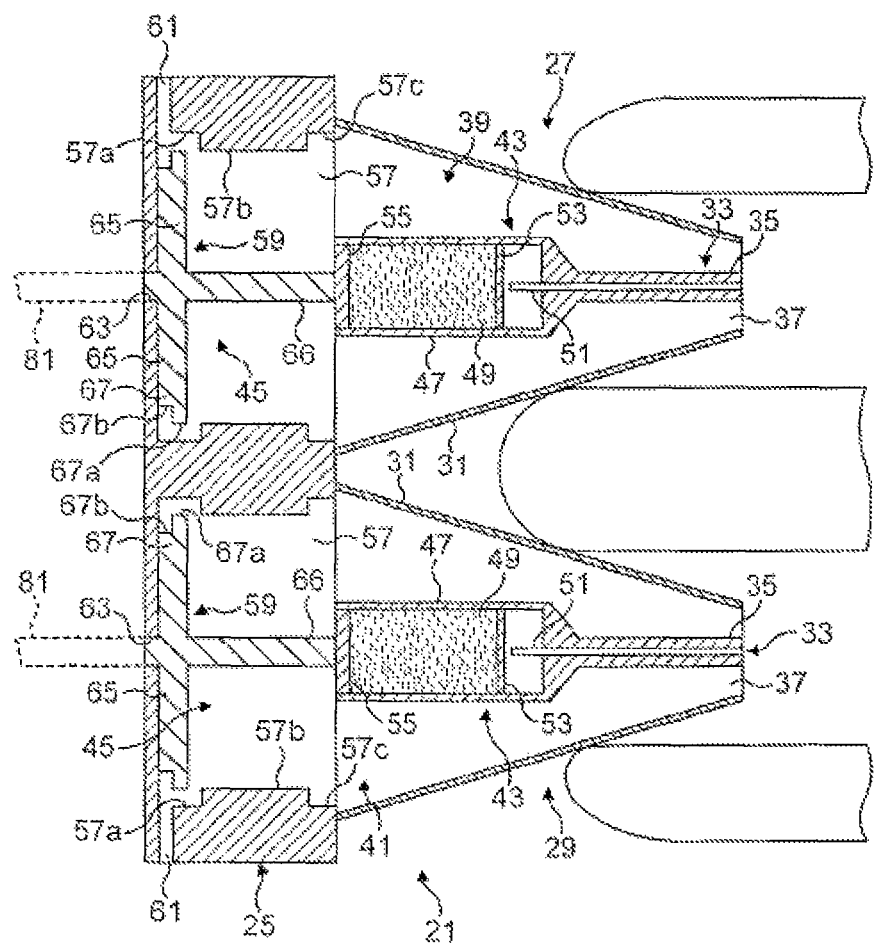
Figure 6B:
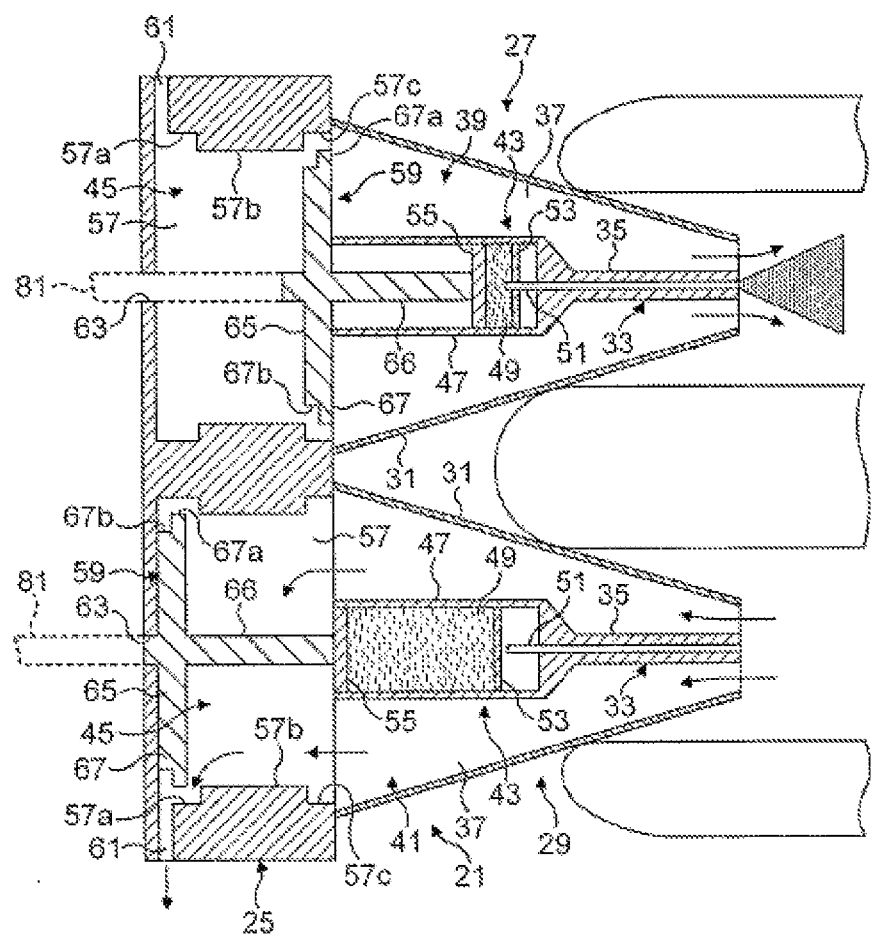

With this configuration, as illustrated in FIGS. 6(b) and (c), the forward piston 53 is driven forwardly on the rear piston 55 being driven forwardly, the substance contained between the pistons 53, 55 being substantially incompressible. The forward piston 53 is a puncturable member which is punctured by the needle 51 of the respective nozzle 35 on being driven onto the same, with the needle 51 of the respective nozzle 35 being in fluid communication with the substance contained between the pistons 53, 55 on puncturing the forward piston 53.

In this embodiment the forward piston 53 is spaced from the needle 51 of the respective nozzle 35 by a predetermined distance such that the respective gas supply unit 45 is actuated to commence delivery of a gas flow through the respective delivery channel 37 at least simultaneously with the delivery of substance to the respective nozzle 35, and in a preferred embodiment prior to the delivery of substance to the respective nozzle 35.

In another alternative embodiment each substance supply unit 43 could comprise a powder delivery pump for delivering a metered dose of a dry powder on actuation thereof.

In a further alternative embodiment each substance supply unit 43 could comprise a dry powder delivery unit which delivers a metered dose of a substance, as a dry powder, on actuation thereof.

In another alternative embodiment each substance supply unit 43 could comprise an aerosol canister for delivering a metered volume of a propellant or the like, containing a substance, either as a suspension or solution.

Figure 6C:
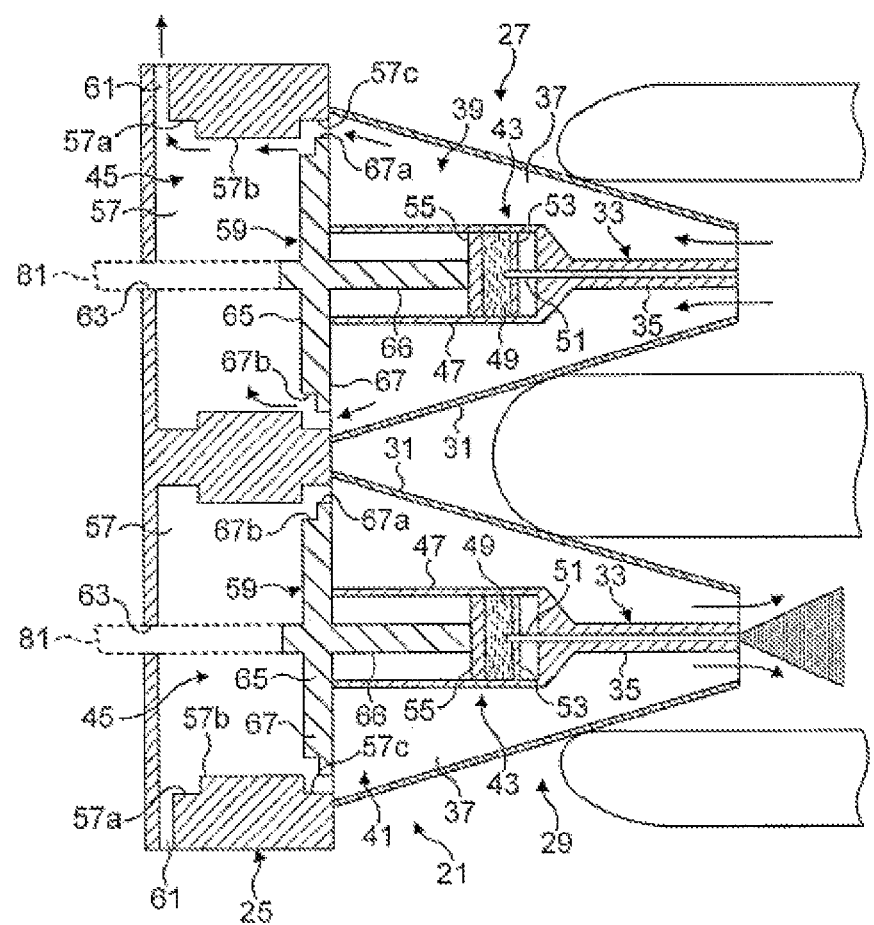
Figure 6D:
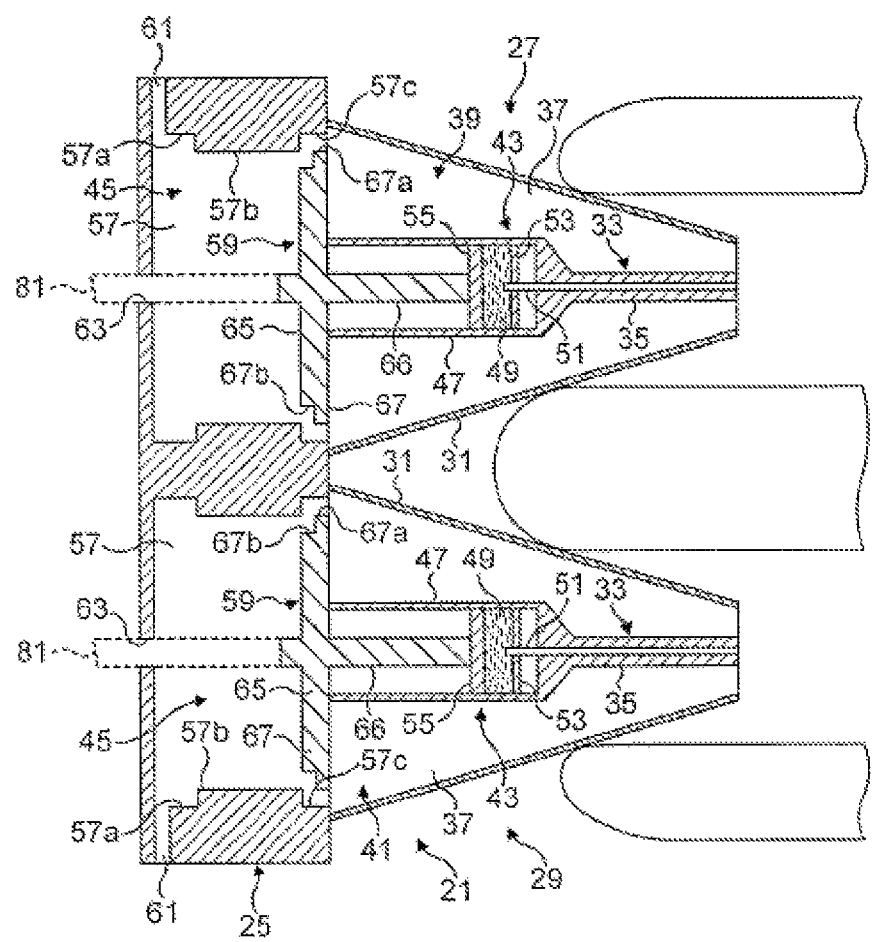

Each gas supply unit 45 comprises a cylinder 57, in this embodiment defined by the main body 25 and being open at the forward end and bounded at the rear end by a rear wall of the main body 25, and a piston 59 which is coupled to the rear piston 55 of the respective substance supply unit 43 and movably disposed within the cylinder 57 between a first, non-actuated position and a second, actuated position such as to drive a volume of gas, in this embodiment about 5 ml, through the respective delivery channel 37 on actuation thereof. FIGS. 6(b) and 6(c) illustrate the actuation of the gas supply unit 45 of respective ones of the first and second delivery units 39, 41.

The cylinder 57 comprises a first, rear section 57a at which the piston 59 is disposed in the non-actuated position, a second, intermediate section 57b at which the piston 59 is disposed during actuation of the piston 59 and a third, forward section 57c at which the piston 59 is disposed in the actuated position, a port 61 which fluidly connects the rear section 57a to atmosphere, and a clearance hole 63 at the rear end thereof to allow for the extension of a drive rod 81 of a respective drive unit 75, 77 of the actuation unit 23 therethrough in driving the rear piston 55 of the respective substance supply unit 43 and the piston 59 of the respective gas supply unit 45.

In this embodiment the port 61 is configured to set the flow resistance of a gas flow driven through the respective nosepiece unit 27, 29. In a preferred embodiment the port 61 is fluidly connected to a filter which acts to trap any substance driven through the respective nosepiece unit 27, 29.

In this embodiment the clearance hole 63 is configured to be a sealing fit with a drive rod 81 of a respective drive unit 75, 77 of the actuation unit 23, but need not be a sealing fit, as there is no requirement for a sealing fit. In an alternative embodiment the rear wall of the main body 25, which defines the rear end of each cylinder 57, can comprise a resilient material which is deflected by the drive rod 81 of the respective drive unit 75, 77 of the actuation unit 23.

The rear section 57a of the cylinder 57 has a greater radial dimension than the piston 59 such that, when the piston 59 is in the non-actuated position, an annular channel is defined about the piston 59 in fluid communication with the port 61, whereby a gas flow driven into the respective nosepiece unit 27, 29 from the other nosepiece unit 27, 29 is vented to atmosphere through the port 61. In this embodiment the first and second delivery units 39, 41 are actuated in succession such that the piston 59 of one of the delivery units 39, 41 is in the non-actuated position during actuation of the other of the delivery units 39, 41, thereby providing a flow path through the one nosepiece unit 27, 29.

The intermediate section 57b of the cylinder 57 has the same radial dimension as the piston 59 such that the piston 59 is a sealing fit therein, whereby a gas flow is driven through the respective delivery channel 37 during displacement of the piston 59 thereover. In this embodiment the volume of the gas flow is determined by the length of the intermediate section 57b of the cylinder 57.

The forward section 57c of the cylinder 57 has a greater radial dimension than the piston 59 such that, when the piston 59 is in the actuated position, an annular channel is defined about the piston 59 in fluid communication with the port 61, whereby a gas flow driven into the respective nosepiece unit 27, 29 from the other nosepiece unit 27, 29 is vented to atmosphere through the port 61. In this embodiment, where the first and second delivery units 39, 41 are actuated in succession, the piston 59 of the other of the delivery units 39, 41, that is, the delivery unit 39, 41 which is first actuated, is in the actuated position during actuation of the other of the delivery units 39, 41, thereby providing a flow path to atmosphere through the other nosepiece unit 27, 29.

The piston 59 comprises an annular element 65 and a connecting rod 66 which is coupled to the rear piston 55 of the respective substance supply unit 43. The annular element 65 includes a stepped peripheral edge 67, the peripheral edge 67 including a first, forward section 67a having the same radial dimension as the intermediate section 57b of the cylinder 57 such as to be a sealing fit therewith, and a second, rear section 67b having a smaller radial dimension than the forward section 67a such as to provide an annular flow path about the peripheral edge 67 when the piston 59 is in the actuated position.

In this embodiment the annular element 65 is configured to sealingly engage the rear end of the respective cylinder 57, and thereby close the respective clearance hole 63, when in the non-actuated position.

The interface unit 21 further comprises a mouthpiece unit 69 into which the subject exhales to actuate the actuation unit 23. In this embodiment the mouthpiece unit 69 comprises a mouthpiece 71, here configured to be gripped in the lips of the subject, and a flexible element 73, here a resilient membrane, which is disposed across the rear end of the mouthpiece 71 such as to be acted upon by the exhalation breath of the subject and be deflected thereby. As will be described in more detail hereinbelow, the actuation unit 23 includes a control unit 89 which is actuated by a predetermined deflection of the flexible element 73, which deflection corresponds to the establishment of a predetermined pressure in the oral cavity of the subject sufficient for closure of the oropharyngeal velum.

The actuation unit 23 comprises a housing 74 to which an interface unit 21 is attachable for the treatment of a subject, the interface unit 21 being a disposable unit, with a fresh interface unit 21 being attached to the housing 74 for each subject to be treated. In this embodiment, in providing that all surfaces, which are brought into contact with a subject or contacted by the exhalation breath of a subject, are confined to the interface unit 21, there is no possibility of cross-contamination of treated subjects.

The actuation unit 23 further comprises first and second drive units 75, 77 for actuating the respective ones of the delivery units 39, 41 of the interface unit 21 in response to exhalation by the subject into the mouthpiece 71.

In this embodiment the drive units 75, 77 each comprise an actuator 79 which includes a drive rod 81, the speed and timing of which is controllable to enable control of the delivery profile of the delivered substance. In a preferred embodiment the actuator 79 comprises a pneumatic actuator.

The actuation unit 23 further comprises a detection unit 83 for detecting the exhalation of the subject into the mouthpiece 71 such as to cause closure of the oropharyngeal velum of the subject. In this embodiment the detection unit 83 comprises a pressure sensor 85 for detecting a pressure developed in the mouthpiece 71, the pressure sensor 85 including a sensing element 87 for sensing the deflection of the resilient element 73 of the mouthpiece unit 69 on exhalation by the subject into the mouthpiece 71. In an alternative embodiment, where the mouthpiece 71 is modified to allow for flow therethrough, the detection unit 83 could comprise a flow sensor for detecting a flow rate developed through the mouthpiece 71 on exhalation by the subject into the mouthpiece 71.

The actuation unit 23 further comprises a control unit 89 which is operably connected to the first and second actuation units 75, 77 and the detection unit 83 such as successively to actuate the delivery units 39, 41 of the interface unit 21 on exhalation by the subject into the mouthpiece 71 with sufficient force as to maintain the oropharyngeal velum in the closed position. In this embodiment the timing of the actuation of the actuation units 75, 77 and the delivery profile of the actuation units 75, 77 can be controlled by the control unit 89.

In one embodiment the actuation unit 23 can include means for registering each subject being treated, such as by photograph, or fingerprint or iris recognition. By registering the subjects being treated, an accurate treatment record can be maintained.

In a preferred embodiment the actuation unit 23 can include an over-ride facility to enable the actuation of the actuation units 75, 77 irrespective of the development of an exhalation flow by the subject which is sufficient to close the oropharyngeal velum. Although bi-directional delivery through the nasal cavities of a subject is desirable, this over-ride facility can prove useful where subject compliance is poor, such as in infants, and the need for exhalation is not understood.

Operation of the delivery device is illustrated in FIGS. 6(*a*) to (*d*), where FIG. 6(*a*) illustrates the fitting of the nosepiece units 27, 29 to the respective nostrils of a subject, and, following exhalation by the subject into the mouthpiece 71 of the mouthpiece unit 69, FIGS. 6(*b*) and (*c*) illustrate the successive actuation of the first and second delivery units 39, 41, and FIG. 6(*d*) illustrates the state subsequent to delivery.

Figure 7B:
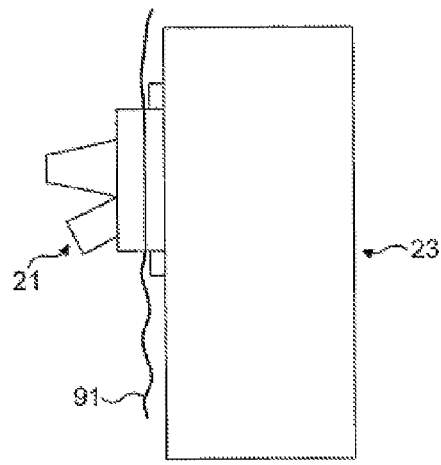

FIGS. 7(*a*) and (*b*) illustrate an interface unit 21 as one modification of the above-described first embodiment.

In this embodiment the interface unit 21 includes protective packaging 91 which acts to maintain the interface unit 21 sterile prior to use, and can also provide protection for the contained substance, where the substance is sensitive to environmental factors, such as moisture and gas uptake, typically oxygen uptake. FIGS. 7(*a*) and (*b*) illustrate the interface unit 21 with the packaging closed and open respectively.

FIG. 8 illustrates an interface unit supply 93 as another modification of the above-described first embodiment.

In this embodiment, instead of the interface units 21 being provided singly, the interface units 21 are mounted on a belt 95 such as to allow for automated or at least semi-automated attachment of the interface units 21 in turn.

In a preferred embodiment the actuation unit 23 can include an advance mechanism which acts to advance each interface unit 21 in turn to the attachment position, with the interface units 21 being guided along a track by the belt 95, whereby the operator is not required to attach the interface units 21, but merely has to perform a supervisory function.

It will be understood that the interface units 21 of the interface unit supply 93 could include protective packaging 91 as in the above-described modification.

FIGS. 9 to 12 illustrate a nasal delivery device in accordance with a second embodiment of the present invention.

The delivery device comprises an interface unit 121 for fitting to a subject and containing the substance to be delivered, and an actuation unit 123 to which the interface unit 121 is attached to enable the delivery of the substance from the interface unit 121 on exhalation by the subject. In this embodiment the interface unit 121 and the actuation unit 123 are disposable components, and the actuation unit 123, in being of simple construction, enables use in regions which cannot be readily accessed by medical personnel, for example, in remote regions, regions of devastation or regions of epidemic.

The interface unit 121 comprises a main body 125 for attachment to the actuation unit 123, in this embodiment as a sliding fit. In an alternative embodiment the main body 125 could be configured to be a clip fit to the actuation unit 123. In this embodiment the means of attachment of the interface unit 121 to the actuation unit 123 is configured, here by the provision of differently shaped slide features, such as to provide for the attachment of the interface unit 121 to the actuation unit 123 in the correct orient.

The interface unit 121 further comprises first and second nosepiece units 127, 129 for fitting to respective ones of the nostrils of a subject.

The nosepiece units 127, 129 each comprise a cuff member 131, in this embodiment a frusto-conical element, for positioning the respective nosepiece unit 127, 129 in a nasal cavity of the subject and providing a fluid-tight seal therewith, and an outlet unit 133 for delivering substance into the respective nasal cavity of the subject.

Each outlet unit 133 comprises a nozzle 135 from which substance is delivered into the respective nasal cavity of the subject, and a delivery channel 137 through which a gas flow, in this embodiment separate from the exhalation breath of the subject, is delivered to entrain the substance delivered from the nozzle 135. In an alternative embodiment the interface unit 121 could be configured such that the entraining gas flow is from the exhalation breath of the subject.

In this embodiment the nozzle 135 is configured to provide an aerosol spray. In an alternative embodiment, for the delivery of a liquid, the nozzle 135 could be configured to deliver a liquid jet as a column of liquid.

In this embodiment the nozzle 135 is disposed in the delivery channel 137 co-axially with the same. In this embodiment the delivery channel 137 is an annular channel which surrounds the nozzle 135 such as to define an annular gas flow which entrains the substance delivered from the nozzle 135.

The interface unit 121 further comprises first and second delivery units 139, 141 which are fluidly connected to respective ones of the first and second nosepiece units 127, 129. The delivery units 139, 141 each comprise a substance supply unit 143 for delivering a metered dose of a substance to the respective nozzle 135 and a gas supply unit 145 for delivering a metered volume of a gas, in this embodiment separate to the exhalation breath of the subject, as a gas flow through the respective delivery channel 137. In preferred embodiments the substance comprises a medicament, especially systemic or topical pharmaceuticals, or a vaccine.

In this embodiment each substance supply unit 143 comprises a liquid delivery pump for delivering a metered dose of a substance on actuation thereof, as one of an aerosol spray or a liquid jet as a column of liquid from the respective nozzle 135.

Each substance supply unit 143 comprises a piston unit which comprises a cylinder 147 which defines a chamber 149 and into one, forward end of which a hollow needle 151 extends as an extension of the respective nozzle 135.

Each substance supply unit 143 further comprises first and second pistons 153, 155 which contain a volume of substance therebetween and are movably disposed within the respective chamber 149.

Figure 12A:
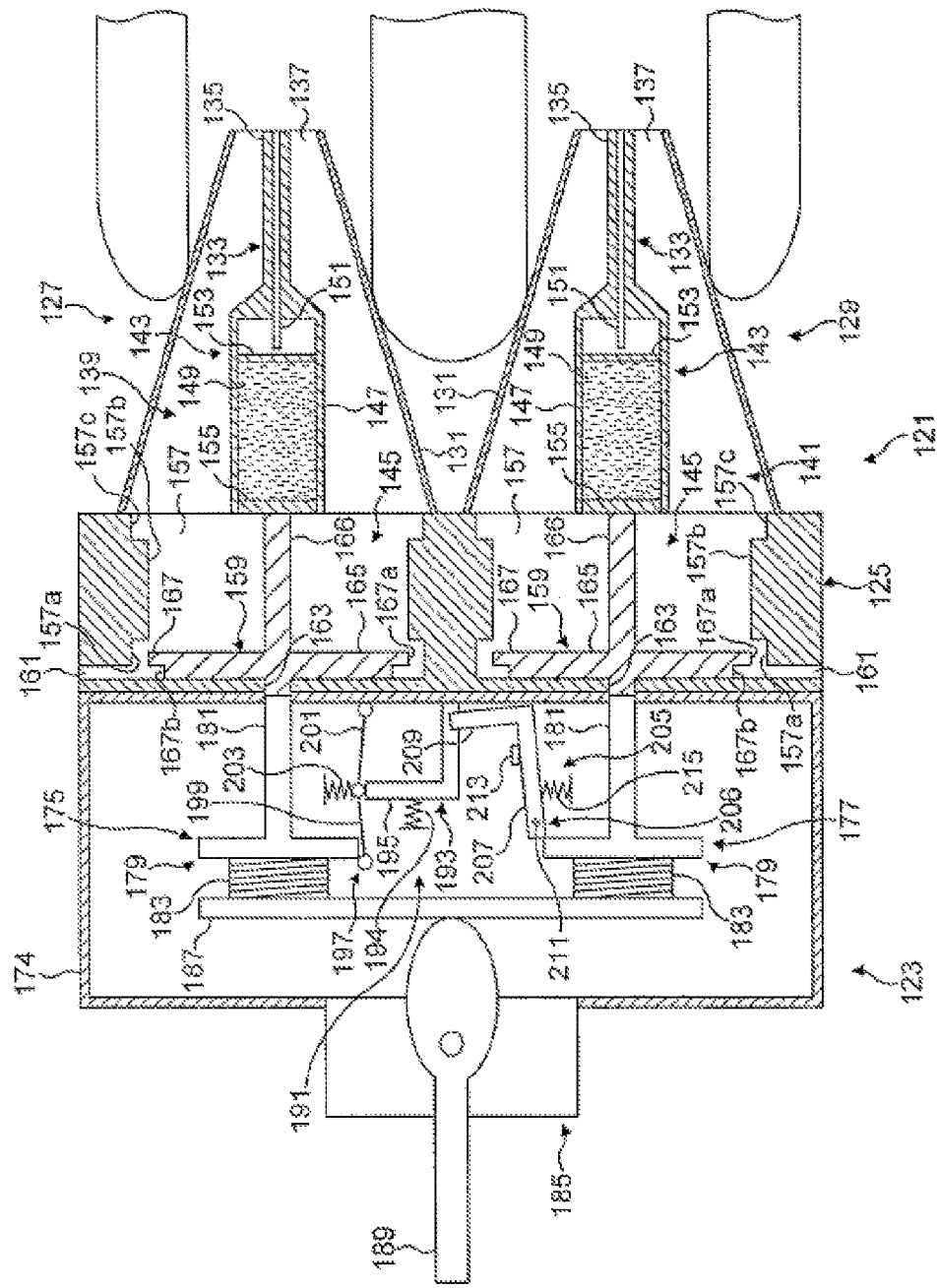
Figure 12B:
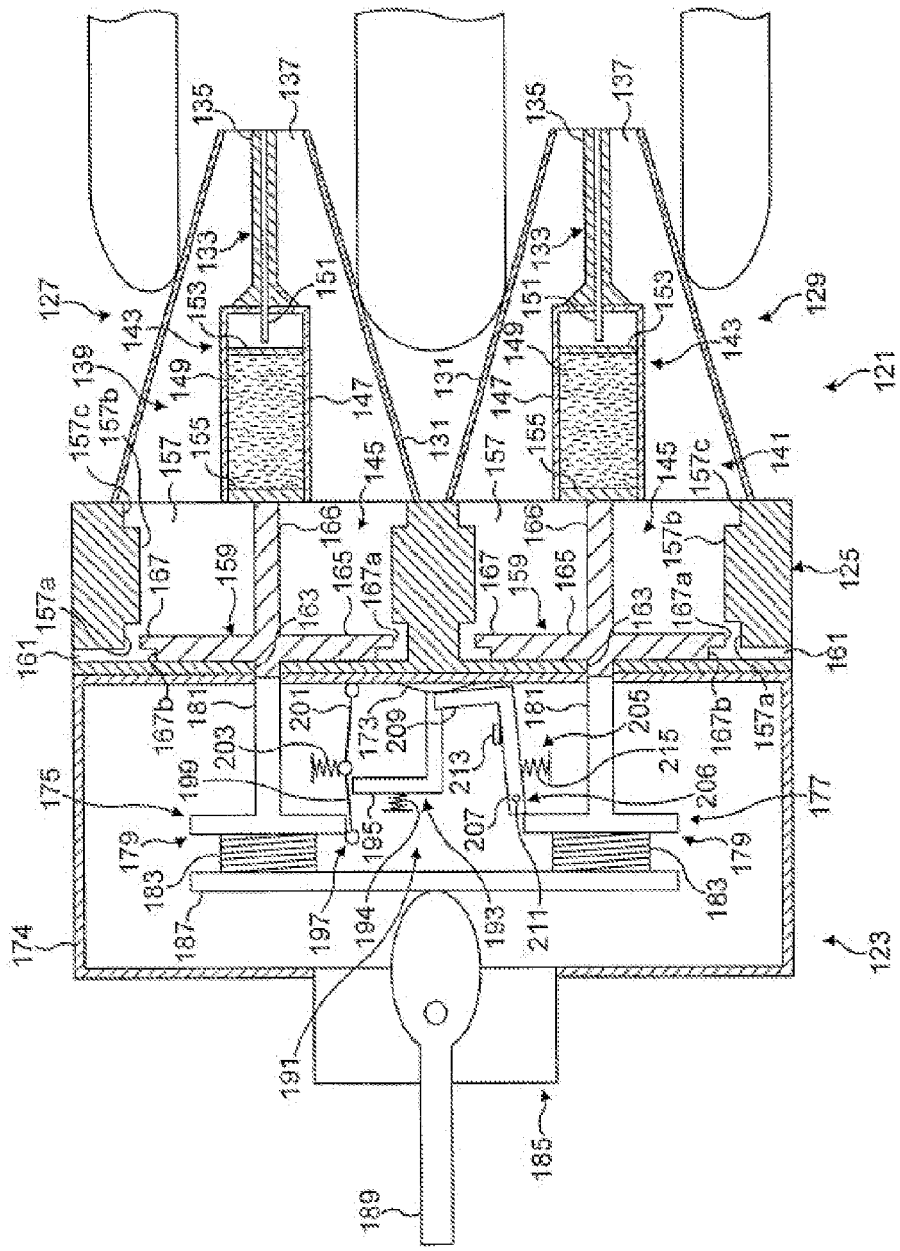
Figure 12C:
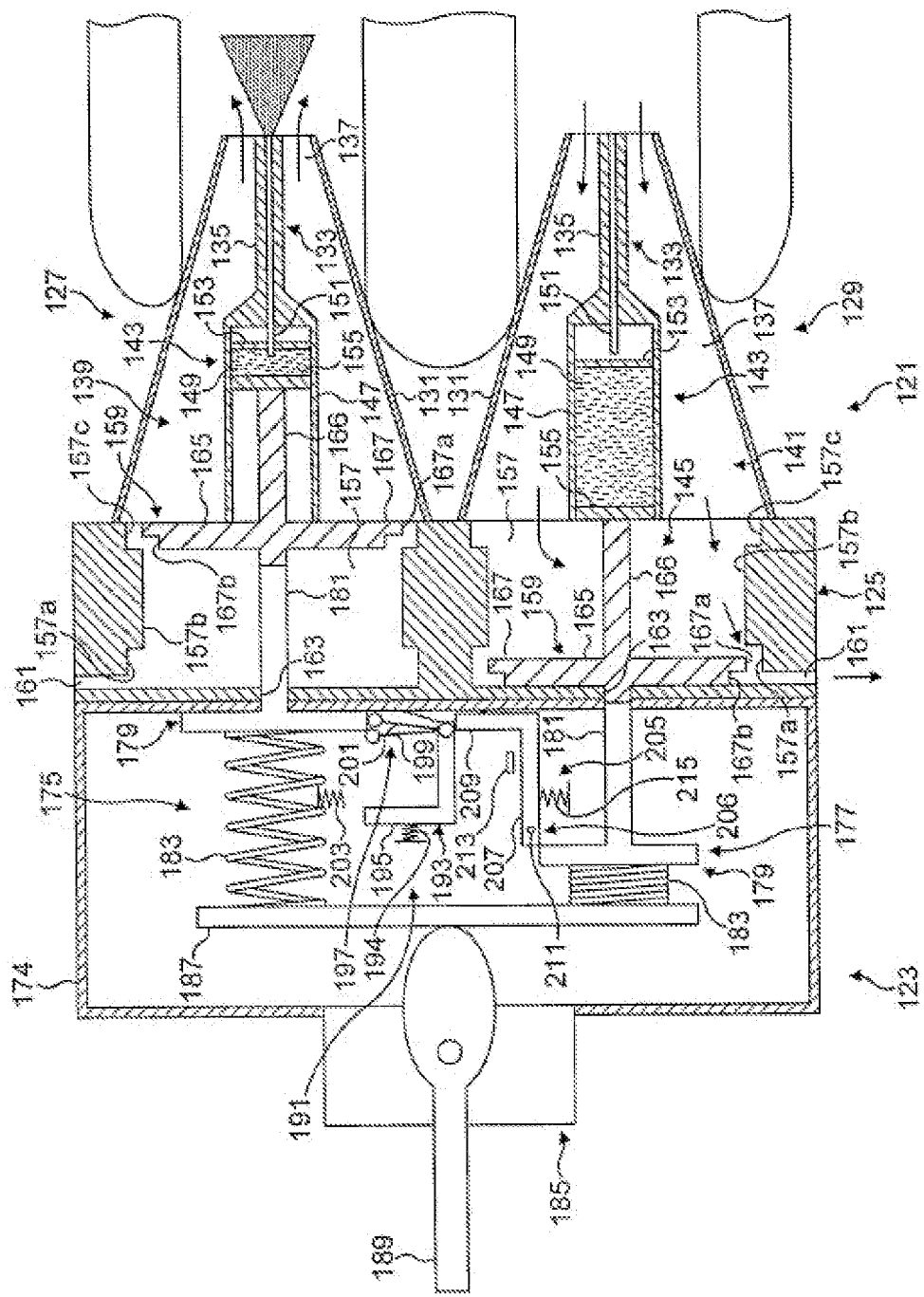

With this configuration, as illustrated in FIGS. 12(c) and (d), the forward piston 153 is driven forwardly on the rear piston 155 being driven forwardly, the substance contained between the pistons 153, 155 being substantially incompressible. The forward piston 153 is a puncturable member which is punctured by the needle 151 of the respective nozzle 135 on being driven onto the same, with the needle 151 of the respective nozzle 135 being in fluid communication with the substance contained between the pistons 153, 155 on puncturing the forward piston 153.

In this embodiment the forward piston 153 is spaced from the needle 151 of the respective nozzle 135 by a predetermined distance such that the respective gas supply unit 145 is actuated to commence delivery of a gas flow through the respective delivery channel 137 at least simultaneously with the delivery of substance to the respective nozzle 135, and in a preferred embodiment prior to the delivery of substance to the respective nozzle 135.

In another alternative embodiment each substance supply unit 143 could comprise a powder delivery pump for delivering a metered dose of a dry powder on actuation thereof.

In a further alternative embodiment each substance supply unit 143 could comprise a dry powder delivery unit which delivers a metered dose of a substance, as a dry powder, on actuation thereof.

In another alternative embodiment each substance supply unit 143 could comprise an aerosol canister for delivering a metered volume of a propellant or the like, containing a substance, either as a suspension or solution.

Each gas supply unit 145 comprises a cylinder 157, in this embodiment defined by the main body 125 and being open at the forward end and closed at the rear end by a rear wall of the main body 125, and a piston 159 which is coupled to the rear piston 155 of the respective substance supply unit 143 and movably disposed within the cylinder 157 between a first, non-actuated position and a second, actuated position such as to drive a volume of gas, in this embodiment about 5 ml, through the respective delivery channel 137 on actuation thereof. FIGS. 12(c) and (d) illustrate the actuation of the gas supply unit 145 of respective ones of the first and second delivery units 139, 141.

The cylinder 157 comprises a first, rear section 157a at which the piston 159 is disposed in the non-actuated position, a second, intermediate section 157b at which the piston 159 is disposed during actuation of the piston 159 and a third, forward section 157c at which the piston 159 is disposed in the actuated position, a port 161 which fluidly connects the rear section 157a to atmosphere, and a clearance hole 163 at the rear end thereof to allow for the extension of a driving rod 181 of a respective drive unit 175, 177 of the actuation unit 123 therethrough in driving the rear piston 155 of the respective substance supply unit 143 and the piston 159 of the respective gas supply unit 145.

In this embodiment the port 161 is configured to set the flow resistance of a gas flow driven through the respective nosepiece unit 127, 129. In a preferred embodiment the port 161 is fluidly connected to a filter which acts to trap any substance driven through the respective nosepiece unit 127, 129.

In this embodiment the clearance hole 163 is configured to be a sealing fit with a driving rod 181 of a respective drive unit 175, 177 of the actuation unit 123, but in other embodiments need not be a sealing fit, as there is no requirement for a sealing fit. In an alternative embodiment the rear wall of each cylinder 157 can comprise a resilient material which is deflected by the drive rod 181 of the respective drive unit 175, 177 of the actuation unit 123 in driving the rear piston 155 of the respective substance supply unit 143 and the piston 159 of the respective gas supply unit 145.

The rear section 157a of the cylinder 157 has a greater radial dimension than the piston 159 such that, when the piston 159 is in the non-actuated position, an annular channel is defined about the piston 159 in fluid communication with the port 161, whereby a gas flow driven into the respective nosepiece unit 127, 129 from the other nosepiece unit 127, 129 is vented to atmosphere through the port 161. In this embodiment the first and second delivery units 139, 141 are actuated in succession such that the piston 159 of one of the delivery units 139, 141 is in the non-actuated position during actuation of the other of the delivery units 139, 141, thereby providing a flow path through the respective one of the nosepiece units 127, 129.

The intermediate section 157b of the cylinder 157 has the same radial dimension as the piston 159 such that the piston 159 is a sealing fit therein, whereby a gas flow is driven through the respective delivery channel 137 during displacement of the piston 159 thereover. In this embodiment the volume of the gas flow is determined by the length of the intermediate section 157*b* of the cylinder 157.

The forward section 157*c* of the cylinder 157 has a greater radial dimension than the piston 159 such that, when the piston 159 is in the actuated position, an annular channel is defined about the piston 159 in fluid communication with the port 161, whereby a gas flow driven into the respective nosepiece unit 127, 129 from the other nosepiece unit 127, 129 is vented to atmosphere through the port 161. In this embodiment, where the first and second delivery units 139, 141 are actuated in succession, the piston 159 of the other of the delivery units 139, 141, that is, the delivery unit 139, 141 which is first actuated, is in the actuated position during actuation of the other of the delivery units 139, 141, thereby providing a flow path through the other nosepiece unit 127, 129.

The piston 159 comprises an annular element 165 and a connecting rod 166 which is coupled to the rear piston 155 of the respective substance supply unit 143. The annular element 165 includes a stepped peripheral edge 167, the peripheral edge 167 including a first, forward section 167*a* having the same radial dimension as the intermediate section 157*b* of the cylinder 157 such as to be a sealing fit therewith, and a second, rear section 167*b* having a smaller radial dimension than the forward section 167*a* such as to provide an annular flow path about the peripheral edge 167 when the piston 159 is in the actuated position.

In this embodiment the annular element 165 is configured to sealingly engage the rear end of the respective cylinder 157, and thereby close the respective clearance hole 163, when the piston 159 is in the non-actuated position.

The interface unit 121 further comprises a mouthpiece unit 169 into which the subject exhales to actuate the actuation unit 123. In this embodiment the mouthpiece unit 169 comprises a mouthpiece 171, here configured to be gripped in the lips of the subject, and a flexible element 173, here a resilient membrane, which is disposed across the rear end of the mouthpiece 171 such as to be acted upon by the exhalation breath of the subject and be deflected thereby. As will be described in more detail hereinbelow, the actuation unit 123 includes a trigger mechanism 191 which is actuated by a predetermined deflection of the flexible element 173, which deflection corresponds to the establishment of a predetermined pressure in the oral cavity of the subject sufficient for closure of the oropharyngeal velum. FIG. 12(*b*) illustrates the state where a subject is exhaling into the mouthpiece 171 of the mouthpiece unit 169 such as to cause deflection of the flexible element 173, but prior to the actuation of the delivery units 139, 141.

The actuation unit 123 comprises a housing 174 to which an interface unit 121 is attachable for the treatment of a subject.

The actuation unit 123 further comprises first and second drive units 175, 177 which are actuatable to actuate respective ones of the delivery units 139, 141 in response to exhalation by the subject. FIGS. 12(*b*) and (*e*) illustrate the first and second drive units 175, 177 in respective ones of the loaded, but non-actuated and actuated configurations.

The drive units 175, 177 each comprise a drive member 179 which is movable between a first, rest position in which the respective delivery unit 139, 141 is in the non-actuated position and a second, actuated position in which the piston 159 of the respective gas supply unit 145 and the rear piston 155 of the respective substance supply unit 143 are advanced to the actuated position. In this embodiment the drive member 179 includes a drive rod 181 which extends through the respective clearance aperture 163 in the main body 125.

The drive units 175, 177 each further comprise a load biasing element 183, in this embodiment a resilient element, particularly a compression spring, for biasing the respective drive member 179 in an actuating direction when in the rest position.

The actuation unit 123 further comprises a loading assembly 185 for commonly loading the load biasing element 183 of each of the drive units 175, 177 such as to bias the drive member 179 of each of the drive units 175, 177 when in the rest position with an actuation force.

The loading assembly 185 comprises a loading block 187 which is commonly coupled to the load biasing elements 183 of the drive units 175, 177, and a loading member 189, in this embodiment a lever, for moving the loading block 187 between a first, inoperative position in which the load biasing elements 183 are not loaded thereby, and a second, operative position in which the load biasing elements 183, when restrained, load the respective drive members 179 with the actuation force.

The actuation unit 123 further comprises a trigger mechanism 191 which is configured normally to lock the drive members 179 of the drive units 175, 177 in the rest position and release the same in succession on exhalation by the subject through the mouthpiece 171, which drive members 179, as loaded by the respective load biasing elements 183, once released act commonly to actuate the respective delivery units 139, 141.

In this embodiment the trigger mechanism 191 is configured to cause successive actuation of the drive units 175, 177 on generation of a predetermined pressure within the mouthpiece 171. FIGS. 12(*c*) and 12(*d*) illustrate the actuation of respective ones of the first and second drive units 175, 177.

In another embodiment the trigger mechanism 191 could be configured to cause the successive actuation of the drive units 175, 177 on generation of a predetermined flow rate through the mouthpiece 171.

The trigger mechanism 191 comprises a release element 193, here a slideable element including a lateral projection 195, which is disposed such as to be engaged by the flexible element 173 of the mouthpiece unit 169 on deflection of the same by the subject exhaling into the mouthpiece 171 at a predetermined pressure and moved from a first, locking position, as illustrated in FIG. 12(*a*), in which the release element 193 acts to lock the trigger mechanism 191 to prevent actuation of the same and a second, release position, as illustrated in FIG. 12(*b*), in which the trigger mechanism 191 is released to enable successive actuation of the delivery units 139, 141.

In this embodiment the trigger mechanism 191 further comprises a biasing element 194, in this embodiment a resilient element, particularly a compression spring, for biasing the release element 193 to the locking position, so as to apply a predetermined actuation force to the flexible element 173 in the mouthpiece 171 of the mouthpiece unit 169 and thereby require a predetermined actuation pressure to be developed in the mouthpiece 171 prior to actuation of the trigger mechanism 191.

The trigger mechanism 191 further comprises a linkage assembly 197 which includes first and second link elements 199, 201, which, when in a locking configuration, act to support the drive member 179 of the first drive unit 175 in the rest position and prevent movement thereof when loaded by the respective load biasing element 183. The linkage assembly 197 is maintained in the locking configuration by the lateral projection 195 of the release element 193 when in the locking position. One of the link elements 199 is pivotally coupled at one end to the drive member 179 of the first drive unit 175, and the other of the link elements 201 is pivotally coupled at one end to the other end of the first link element 199 and at the other end to the housing 174.

The trigger mechanism 191 further comprises a biasing element 203, in this embodiment a resilient element, particularly a compression spring, for biasing the linkage assembly 197 from the locking configuration, such that, on movement of the release element 193 from the locking position to the release position through deflection of the flexible element 173 in the mouthpiece 171 of the mouthpiece unit 169, as illustrated in FIGS. 12(a) and (b), the biasing element 203 acts to collapse the linkage assembly 197, with which collapse the drive member 179 of the first drive unit 175 is driven by the load biasing element 183 thereof to actuate the first delivery unit 139, as illustrated in FIG. 12(c).

The trigger mechanism 191 further comprises a lever assembly 205, which, when in a locking position, as illustrated in FIG. 12(b), acts to support the drive member 179 of the second drive unit 177 in the rest position and prevent movement thereof when loaded by the respective load biasing element 183.

In this embodiment the lever assembly 205 comprises an L-shaped lever 206 which includes first and second arms 207, 209.

Figure 12D:
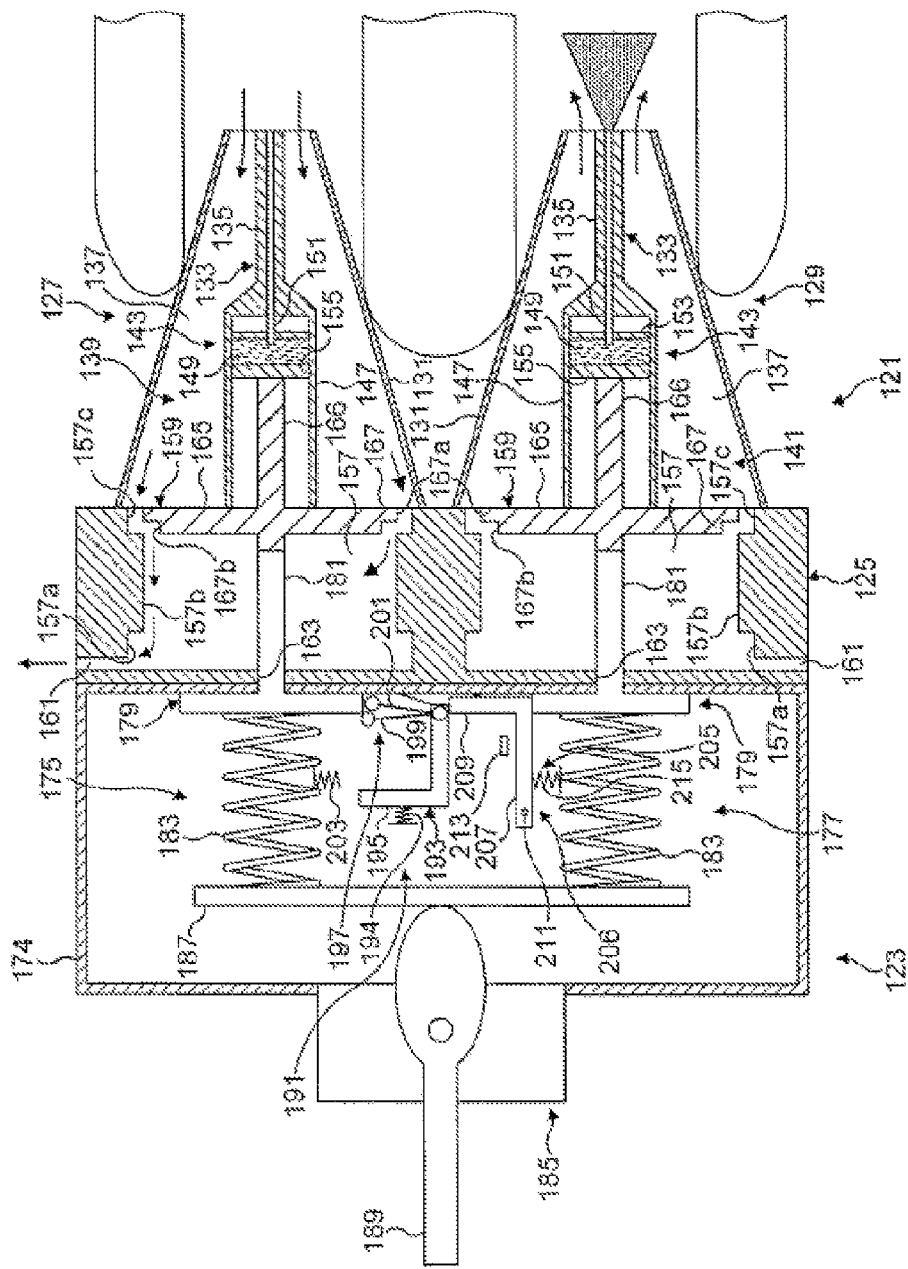

One arm 207 of the lever 206 is mounted at one end thereof about a pivot 211 such as to be rotatable between a locking position, as illustrated in FIG. 12(b), in which the distal end of the one arm 207 engages the drive member 179 of the second drive unit 177 such as to prevent movement thereof when loaded by the respective load biasing element 183, and a release position, as illustrated in FIG. 12(c), in which the lever 206 is rotated such as to release the drive member 179 of the second drive unit 177 from the locking position and thereby actuate the second delivery unit 141, as illustrated in FIG. 12(d).

In this embodiment the lever assembly 205 includes a stop 213 which acts as an abutment against which the lever 206 is supported in the locking position, and a biasing element 215, here a compression spring, for biasing the lever 206 to the locking position.

The other arm 209 of the lever 206 is configured to be engaged by the linkage assembly 197 when the drive member 183 of the first drive unit 175 approaches the actuated position, as illustrated in FIG. 12(c), which engagement acts to rotate the lever 206 to move the lever 206 to the release position, in which position the load biasing element 183 of the second drive unit 177 acts to drive the drive member 179 thereof to the actuated position and thereby actuate the second delivery unit 141.

Figure 12E:
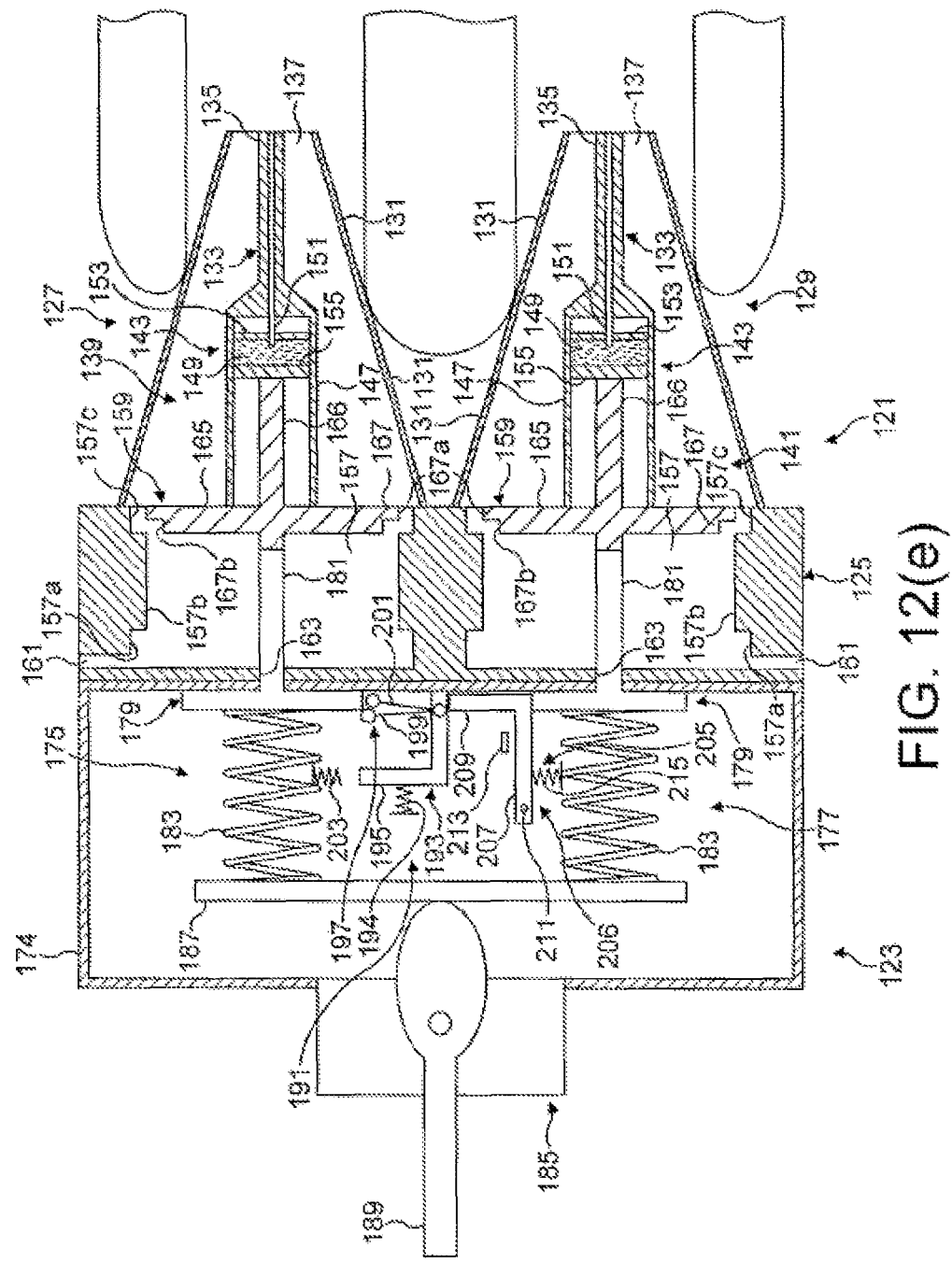

Operation of the delivery device is illustrated in FIGS. 12(a) to (e), where FIG. 12(a) illustrates the priming of the delivery device and the fitting of the nosepiece units 127, 129 to the respective nostrils of a subject, and, following exhalation by the subject into the mouthpiece 171 of the mouthpiece unit 169, FIG. 12(b) illustrates the state where a sufficient pressure has been developed in the mouthpiece 171 as to cause deflection of the flexible element 173 in the mouthpiece 171 and allow actuation of the trigger mechanism 191, FIGS. 12(c) and (d) illustrate the successive actuation of the first and second delivery units 139, 141, and FIG. 12(e) illustrates the state subsequent to delivery.

Finally, it will be understood that the present invention has been described in its preferred embodiments and can be modified in many different ways without departing from the scope of the invention as defined by the appended claims.

For example, the delivery device of the first described embodiment could be modified such that the entraining gas flow is supplied by the actuation unit 23. In this modification, the interface unit 21 is modified to omit the gas supply units 45, with the pistons 59 of the interface unit 21 in this embodiment being modified to omit the annular elements 65 thereof, and the actuation unit 23 is modified to include a gas supply unit for selectively supplying a gas flow to the delivery channels 37 of the nosepiece units 27, 29 through the ports 61, the gas supply unit being configured to vent to atmosphere the other of the ports 61 than to which the gas flow is being supplied. This configuration enables a high flow rate to be developed, where desired. In a preferred embodiment the gas supply unit includes a one-way check valve to prevent back-flow thereinto of gas which has been exposed to the nasal airway of a subject.

In another modification, the interface units 21, 121 of the described embodiments can be configured such as to allow the interface units 21, 121 to be broken along a line between the nosepiece units 27, 29, 127, 129, and thereby allow for the separation of the delivery units 39, 41, 139, 141. In this way, the delivery units 39, 41, 139, 141 can be used to deliver single doses of substance to subjects where an actuation unit 23, 123 is not available.

In a further modification, the interface units 21, 121 can be modified to omit the rear wall of the main body 25, 125 adjacent the gas supply units 45, 145 such as to allow for the manual actuation of the delivery units 39, 41, 139, 141 by depression of the respective piston 59, 159. Such manual actuation of the delivery units 39, 41, 139, 141 would also be possible where the rear wall of the main body 25, 125 adjacent the gas supply units 45, 145 is a flexible element, typically a resilient element, or where the pistons 59, 159 include an actuation rod which extends through the respective clearance aperture 63, 163, with manual actuation of the delivery units 39, 41, 139, 141 being achieved by depression of the respective actuation rod. This modification would also extend to delivery units 39, 41, 139, 141 which include no piston 59, 159.

In a yet further modification, the interface units 21, 121 can include only one nosepiece unit 27, 29, 127, 129 and associated delivery unit 39, 41, 139, 141. In one embodiment the mouthpiece 71, 171 can be fluidly connected to the delivery channel 37, 137 of the one nosepiece unit 27, 29, 127, 129, with the exhalation breath of a subject providing the entraining gas flow. Such an embodiment provides for both automated actuation by an actuation unit 23, 123 where deflection of the flexible element 73, 173 of the mouthpiece unit 69, 169 acts to actuate the actuation unit 23, 123, and manual actuation where the subject simultaneously exhales and manual actuates a delivery unit 39, 41, 139, 141.

In the described embodiments the mouthpieces 71, 171 are configured to be gripped in the lips of a subject. In alternative embodiments the mouthpieces 71, 171 could be configured to be gripped by the teeth of a subject and sealed by the lips of the subject. In preferred embodiments the mouthpieces 71, 171 could be specifically configured to have one or both of a shape or geometry which allows the delivery devices to be gripped repeatedly in the same position, thereby providing for the respective nosepiece units 27, 29, 127, 129 to be reliably inserted in the same position in the nasal cavity.

In preferred embodiments the delivery units are configured to deliver substance through one nostril of a subject at such a pressure as to flow around the posterior margin of the nasal septum and out of the other nostril of the subject, thereby achieving bi-directional delivery through the nasal cavities as disclosed in WO-A-00/51672. In alternative embodiments the delivery units could be configured to deliver substance at a reduced pressure which is not sufficient to achieve bi-directional delivery through the nasal cavities. Such embodiments are still advantageous as compared to known delivery devices in providing for velum closure.

I claim:

1. A nasal delivery device for delivering a substance to a nasal airway of a subject, comprising:
    an interface unit configured to be attachable to an actuation unit, wherein the interface unit is attachable to the actuation unit in a first unaligned position and is movable to a second aligned position, wherein the interface unit is actuatable only in the aligned position;
    the interface unit including a nosepiece unit, a mouthpiece and a delivery unit, the nosepiece unit configured for fitting to a respective nostril of the subject and the delivery unit including a substance supply unit actuatable to deliver the substance to the nosepiece unit.

2. The delivery device of claim 1, wherein the substance is a powder.

3. The delivery device of claim 1, wherein the substance is a liquid.

4. The delivery device of claim 1, wherein the interface unit is a single integral unit.

5. The delivery device of claim 1, wherein the delivery unit is actuated in response to exhalation by the subject.

6. The delivery device of claim 5, wherein the mouthpiece and the nosepiece unit of the interface unit are fluidly connected.

7. The delivery device of claim 1, wherein the interface unit is one of a plurality of interface units each attached to a common support.

8. The delivery device of claim 7, wherein the common support is a belt.

9. A nasal delivery device for delivering a substance to a nasal airway of a subject, comprising:
    an interface unit configured to be attachable to an actuation unit, wherein the interface unit is attachable to the actuation unit in a first unaligned position and is slidably movable through the unaligned position to a second aligned position, wherein the interface unit is actuatable only in the aligned position;
    the interface unit including a nosepiece unit and a delivery unit, the nosepiece unit configured for fitting to a respective nostril of the subject and the delivery unit including a substance supply unit actuatable to deliver the substance to the nosepiece unit.

10. The delivery device of claim 9, wherein the substance is a powder.

11. The delivery device of claim 9, wherein the substance is a liquid.

12. The delivery device of claim 9, wherein the interface unit is a single integral unit.

13. The delivery device of claim 9, wherein the delivery unit is actuated in response to exhalation by the subject.

14. The delivery device of claim 9, wherein the interface unit further comprises a mouthpiece.

15. The delivery device of claim 14, wherein the mouthpiece and the nosepiece unit of the interface unit are fluidly connected.

16. The delivery device of claim 9, wherein the interface unit is one of a plurality of interface units each attached to a common support.

17. The delivery device of claim 16, wherein the common support is a belt.

* * * * *